(12) United States Patent
Denning et al.

(10) Patent No.: US 7,303,868 B2
(45) Date of Patent: Dec. 4, 2007

(54) MUTANT BANK

(75) Inventors: David Wemys Denning, Hale (GB); Jayne Louise Brookman, Glossop (GB); Andre Rickers, Hollingworth (GB); Mike Birch, Worsley (GB)

(73) Assignee: F2G Limited, Manchester (GB)

( * ) Notice: Subject to any disclaimer, the term of this patent is extended or adjusted under 35 U.S.C. 154(b) by 481 days.

(21) Appl. No.: 10/257,213

(22) PCT Filed: Apr. 11, 2001

(86) PCT No.: PCT/GB01/01626

§ 371 (c)(1),
(2), (4) Date: Oct. 10, 2002

(87) PCT Pub. No.: WO01/77295

PCT Pub. Date: Oct. 18, 2001

(65) Prior Publication Data

US 2003/0129733 A1    Jul. 10, 2003

(30) Foreign Application Priority Data

Apr. 11, 2000   (GB) .................. 0008748.6

(51) Int. Cl.
*C12N 1/00*      (2006.01)
*C12N 15/00*    (2006.01)
*C12N 15/10*    (2006.01)
*C12Q 1/02*      (2006.01)
*C12Q 1/68*      (2006.01)

(52) U.S. Cl. .................. 435/6; 435/254.3; 435/440; 435/29; 435/254.1

(58) Field of Classification Search .................. None
See application file for complete search history.

(56) References Cited

U.S. PATENT DOCUMENTS 5,302,527 A * 4/1994 Birkett et al. ............. 435/254.5
5,612,180 A    3/1997 Brown et al.
5,876,931 A    3/1999 Holden
6,783,985 B1 * 8/2004 Roemer et al. ............. 435/440

FOREIGN PATENT DOCUMENTS

EP     0870835     10/1998
WO   WO 99/15644   4/1999

OTHER PUBLICATIONS

Winzeler, et al, Functional Characterization of the *S. cerevisiae* Genome by Gene Deletion and Parallel Analysis, Science 285:901-906, 1999.*
Levadoux, W.L. et al Sequential cold-sensitive mutations in *Aspergillus fumigatus*. II. Analysis by the parasexual cycle. Can. J. Microbiol. 27:295-303, 1981.*
Winzeler et al.. 1999 Science 28 Functions Characterization of the *S. cerevisiae* Genome by Gelen Deletion and Parallel Analysis.
Smith et al., 1996 Science 274, Functional analysis of the Genes of Used Chromosome V by Genetic Foot printing.
Pontecorvo et al. 1953, Adv. Genet. 5: p. 141-238; The Genetics of *Aspergillus nidulas*; Adv. Genet. vol. 5 p. 141-238.
Stromnaes and Garber 1963; Hetercaryosis and the Parasexual Cycle in *Aspergillus fumigatus*, Genetics, 48 653-662.
de Groot et al, 1998; Nature Biotechnology 16: 839-842.
Weidener and d'E Fert, 1998, Current Genetics, vol. 33: 378-385.
Liu et al. 1995 The Plant Journal 8:457-463.
Ross-Macdonald et al, 1997, PNAS USA 94: 190-5.
Smith et al, 1995, PNAS USA 92: 6479-83.
Goebl, Mark G. et al., "Most of the Yeast Genomic Sequences Are Not Essential for Cell Growth and Division", Cell, vol. 48, Sep. 25, 2986, pp. 983-992.

* cited by examiner

*Primary Examiner*—David Guzo
*Assistant Examiner*—Walter Schlapkohl
(74) *Attorney, Agent, or Firm*—Venable LLP; Marina V. Schneller

(57) ABSTRACT

The invention relates to a mutant bank of diploid microorganisms which consists of a population of mutant cells in which at least one cell has a random mutation which disrupts the activity of at least one gene, wherein the micro-organism is inducible into haploid form. The invention further relates to a method of using the mutant bank to identify the genes which contribute to a chosen phenotype.

17 Claims, 13 Drawing Sheets

FIGURE 1. Plasmid pAN7-1
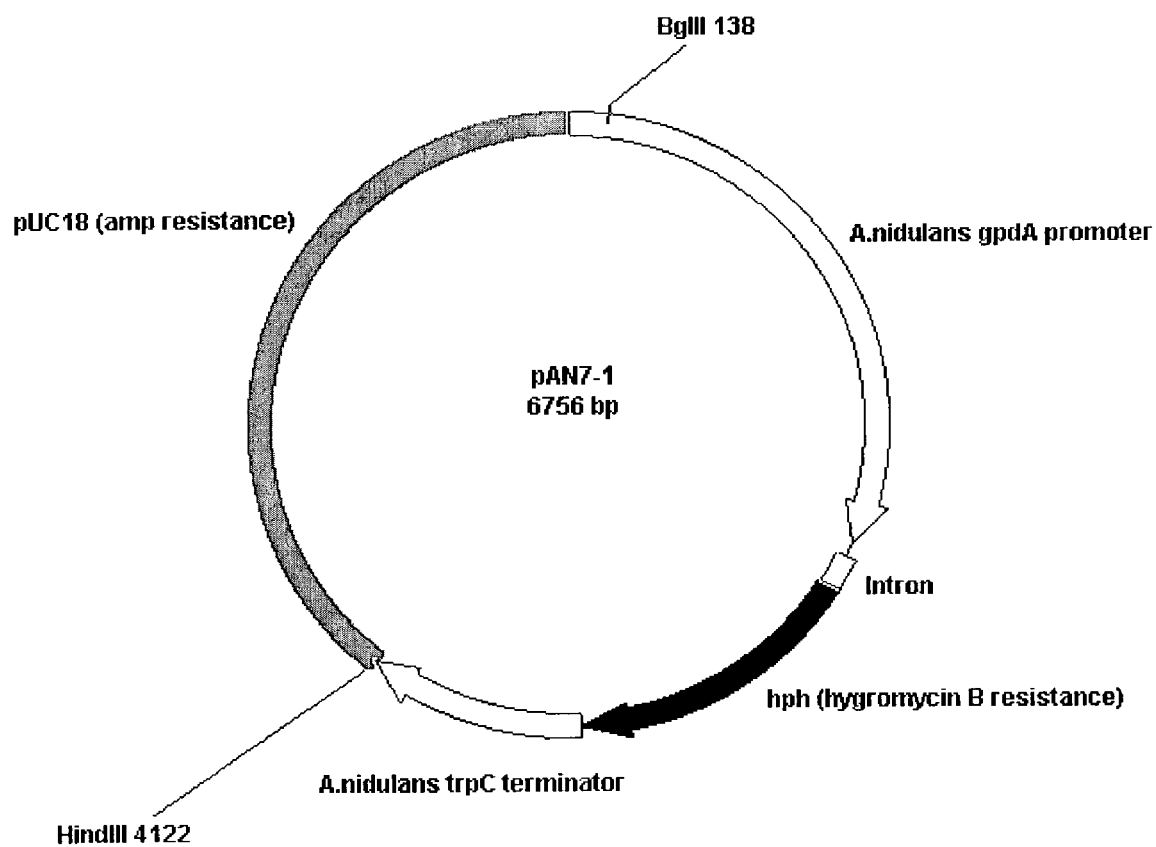

FIGURE 2. Plasmid pRok2
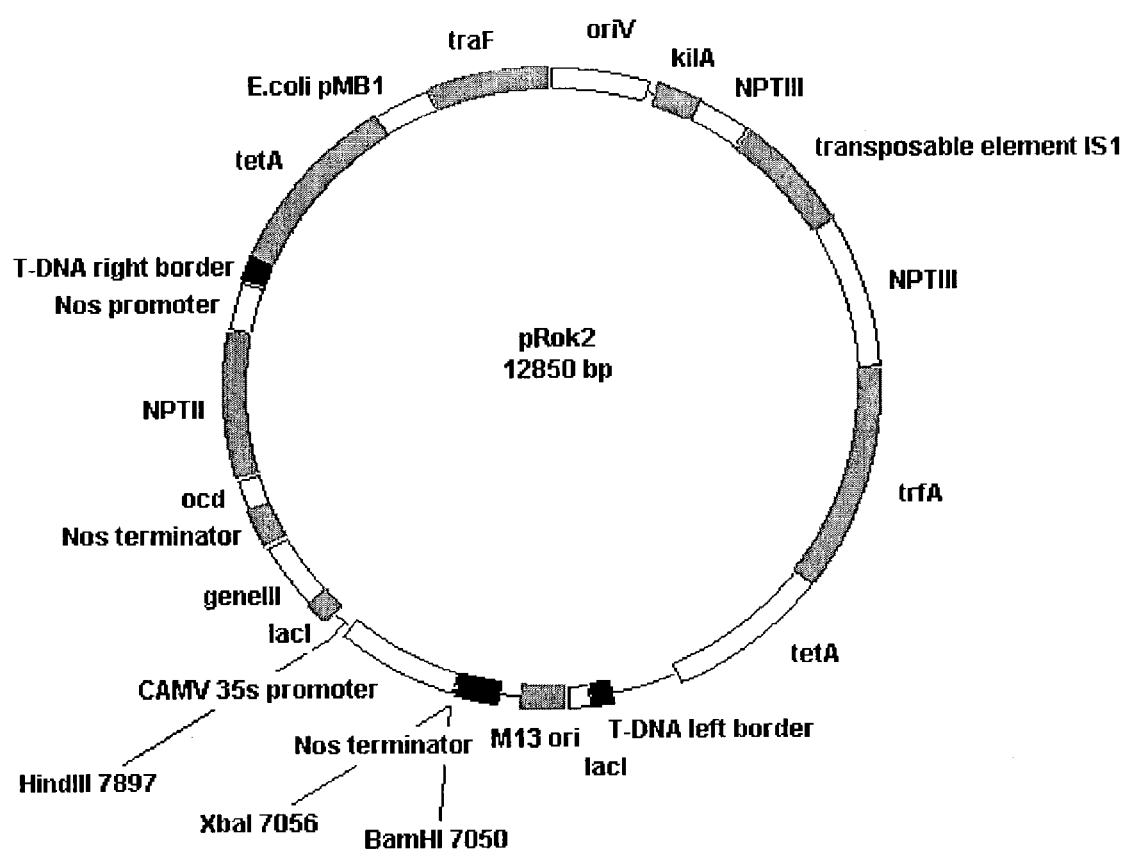

FIGURE 3. Plasmid pRic1
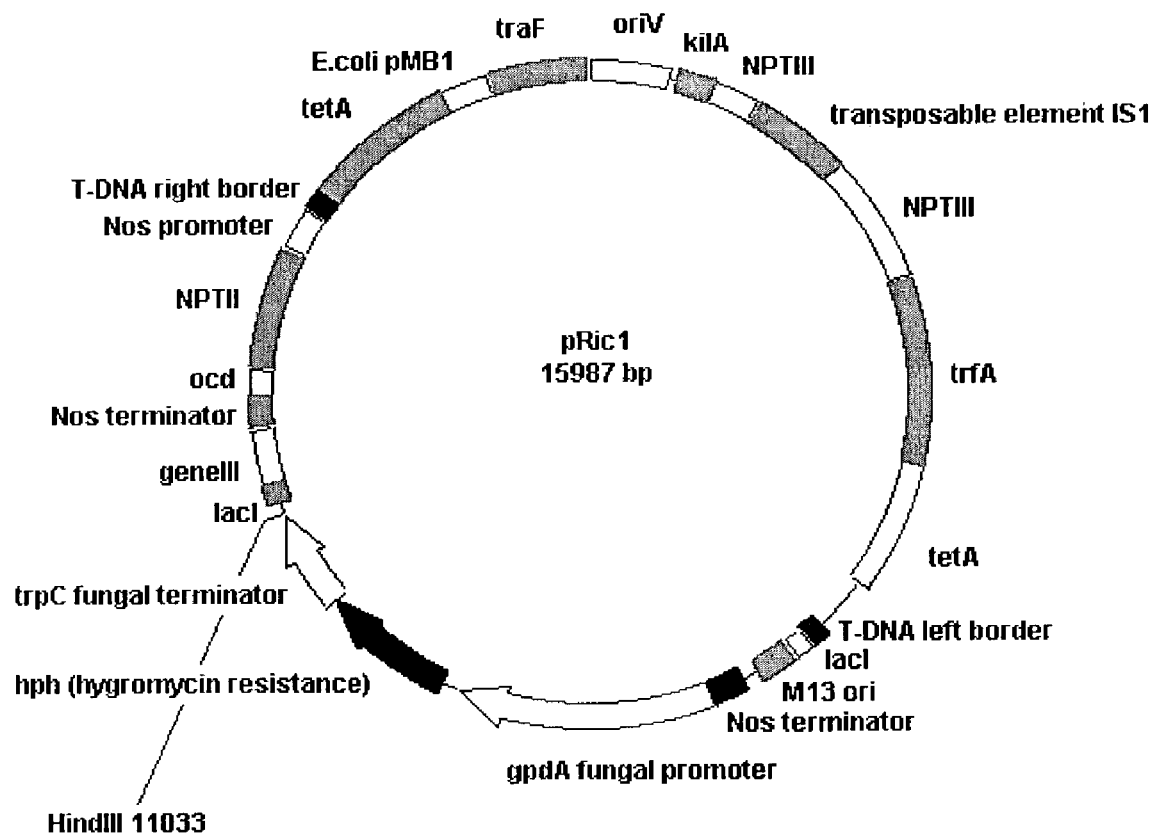

FIGURE 4. Plasmid pUC18
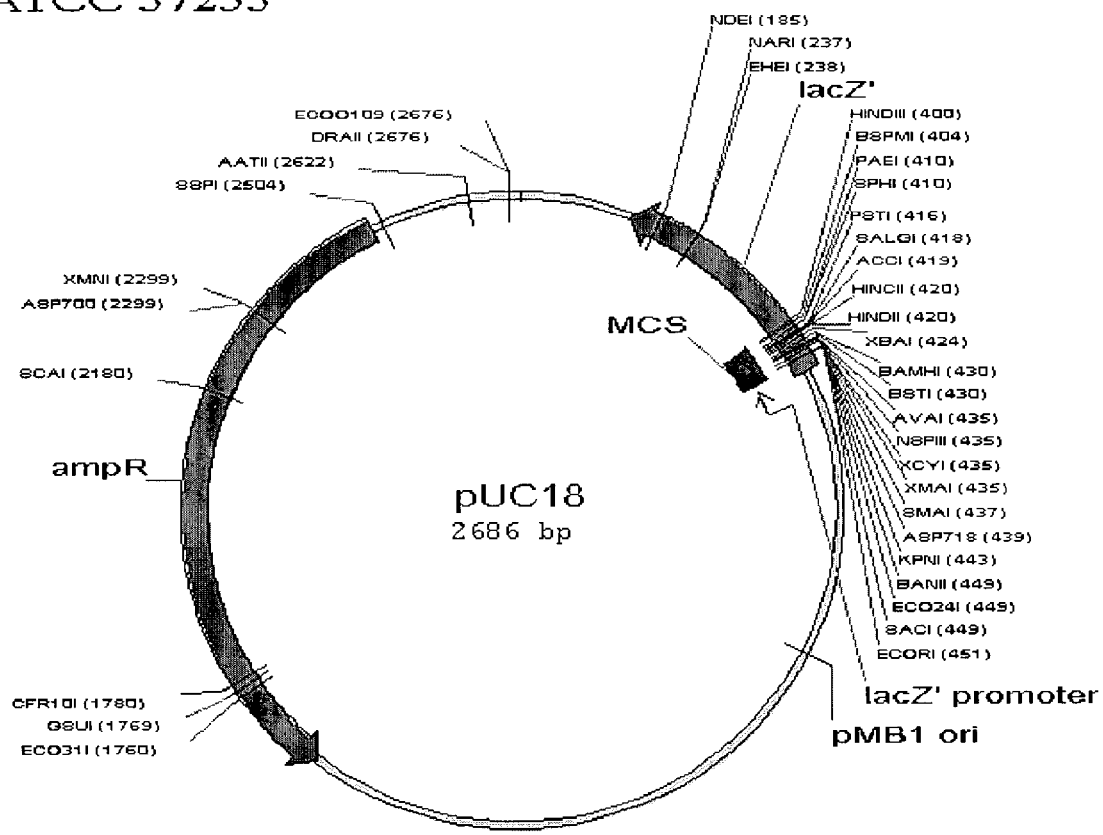

FIGURE 5. Plasmid pRic2
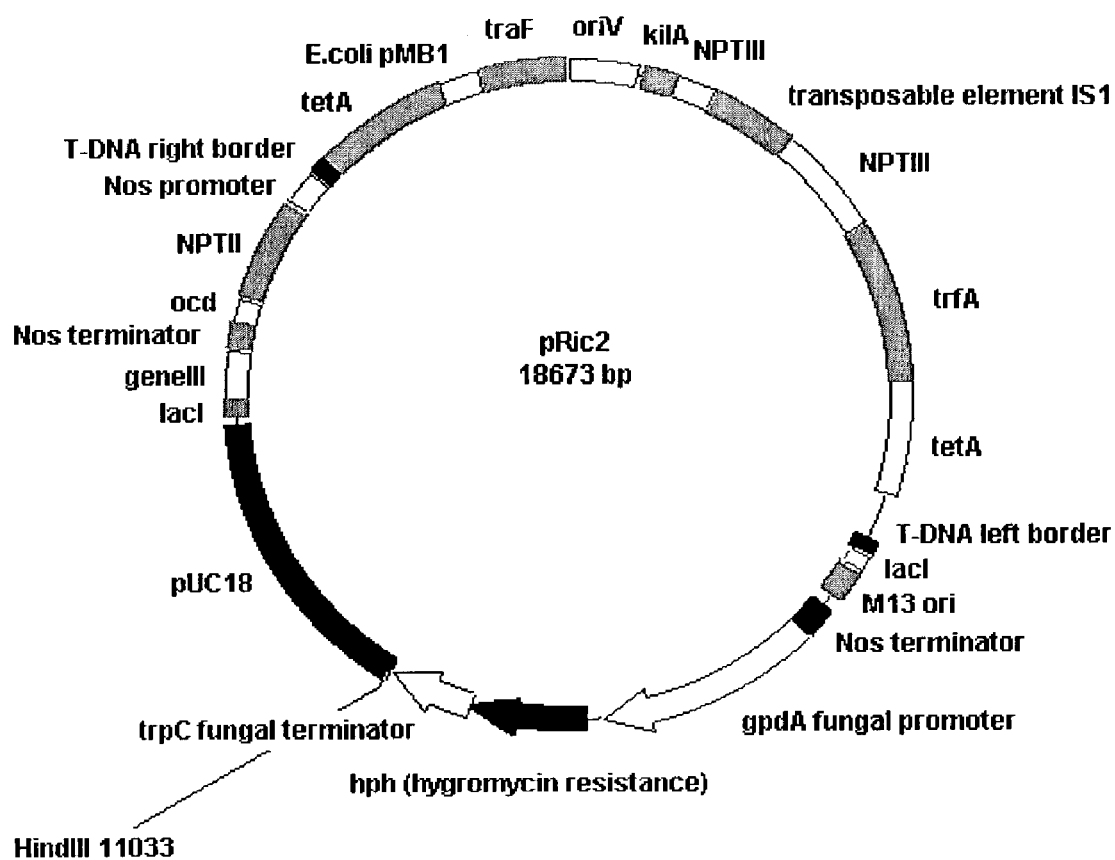

FIGURE 6. Plasmid pRic3
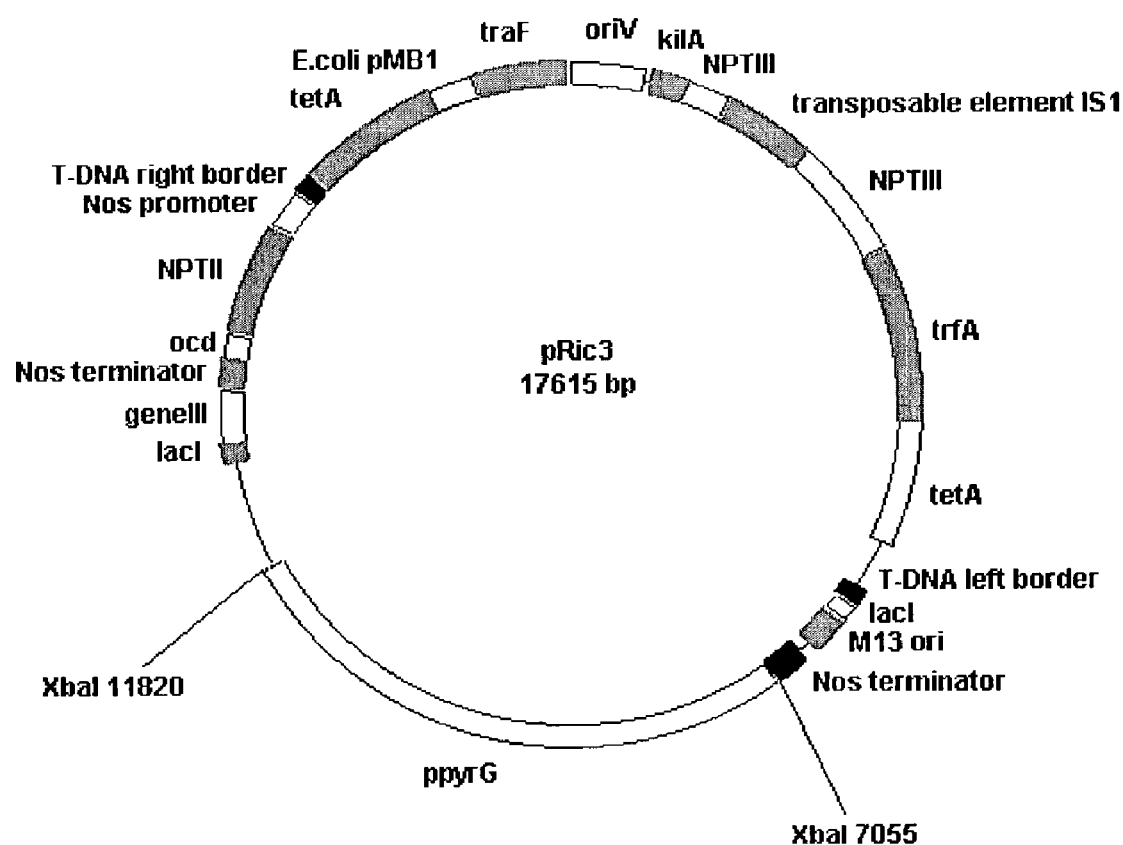

FIGURE 7. Plasmid ppyrG
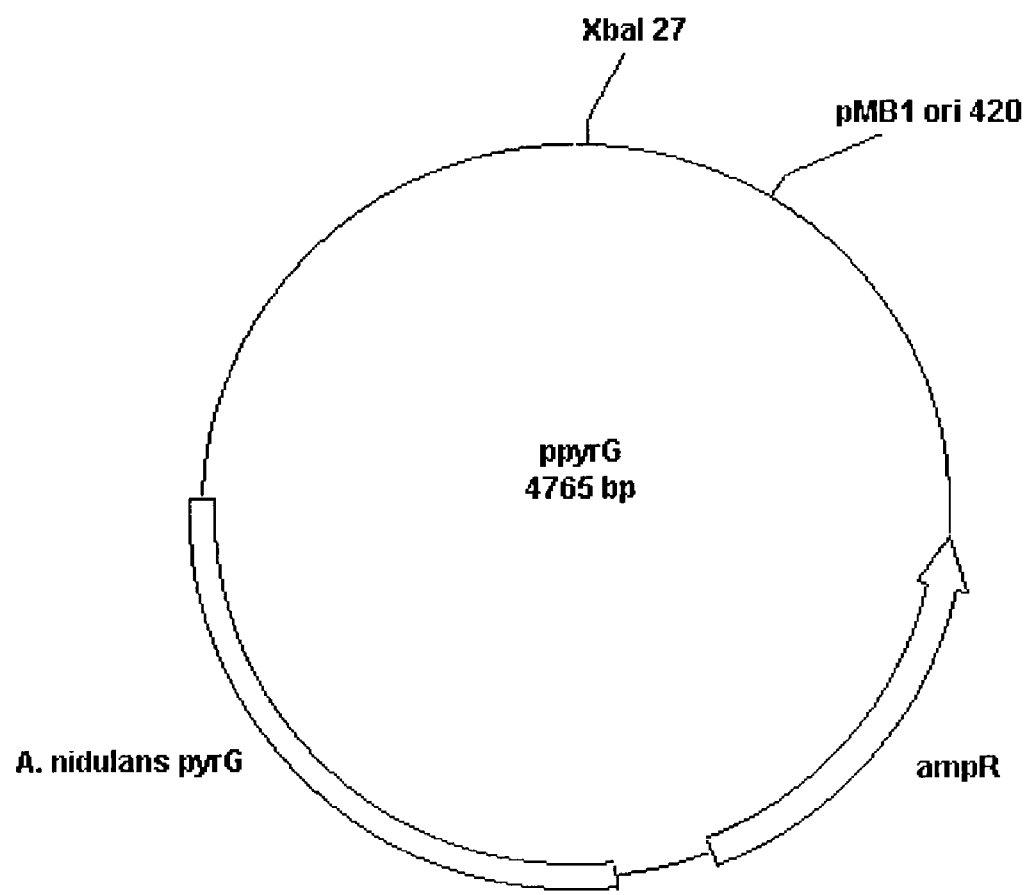

FIGURE 8. Plasmid pCR2.1
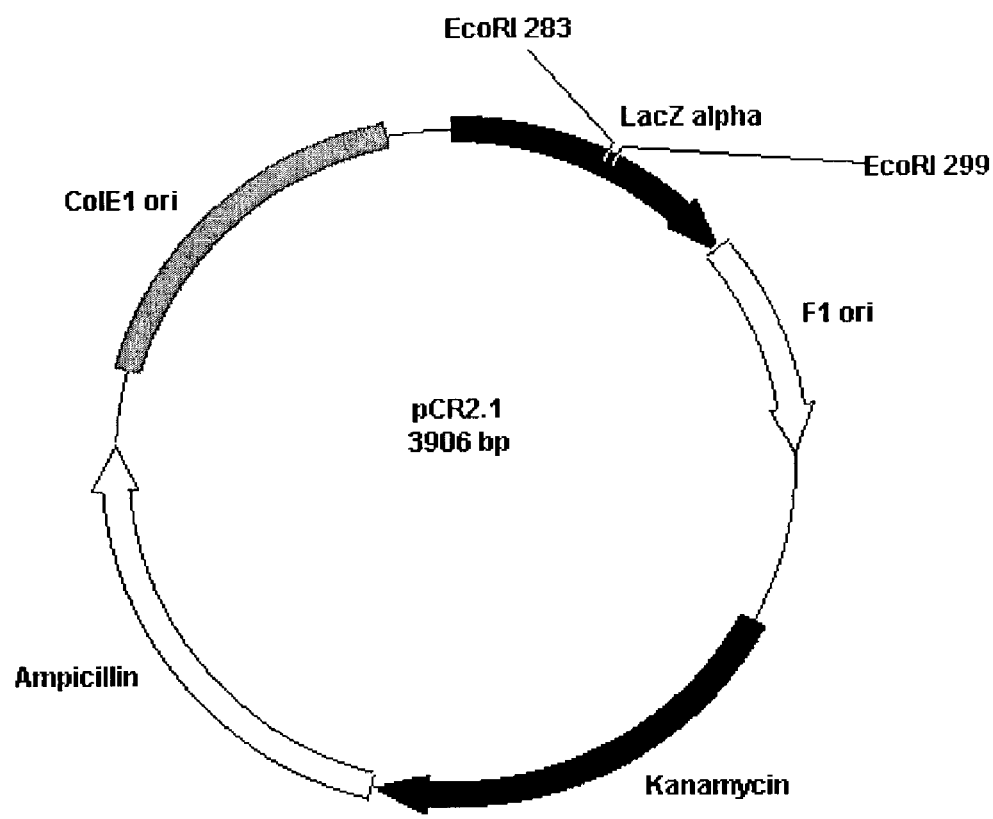

FIGURE 9. Plasmid pTT
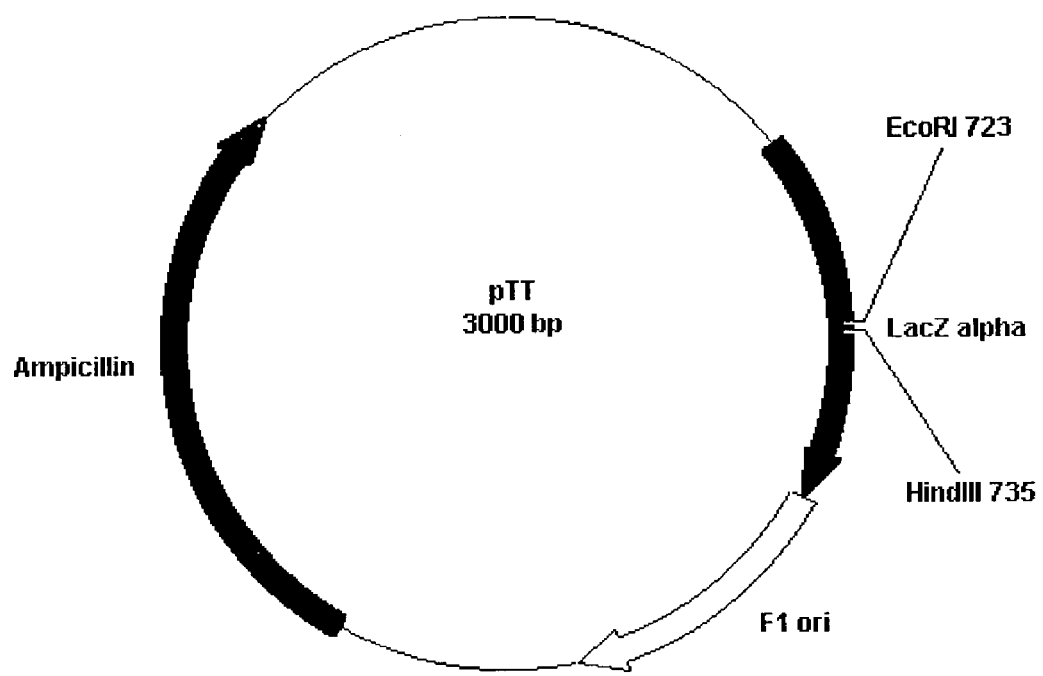

FIGURE 10. Plasmid pMB2
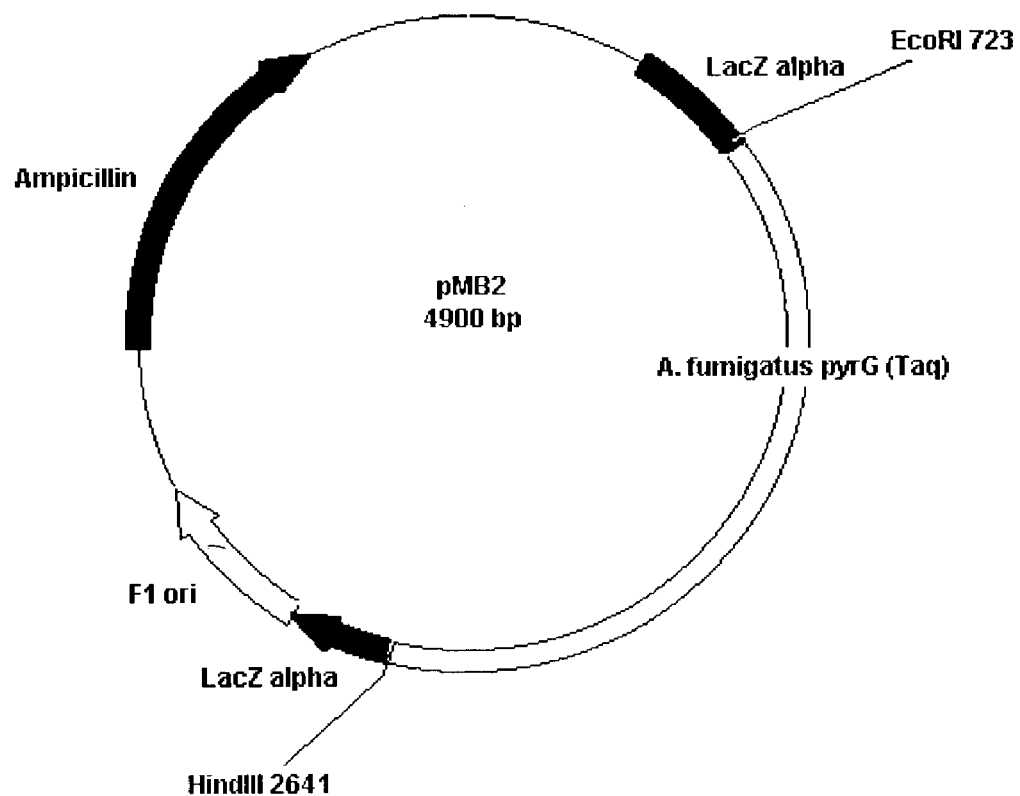

FIGURE 11. Plasmid pMB3
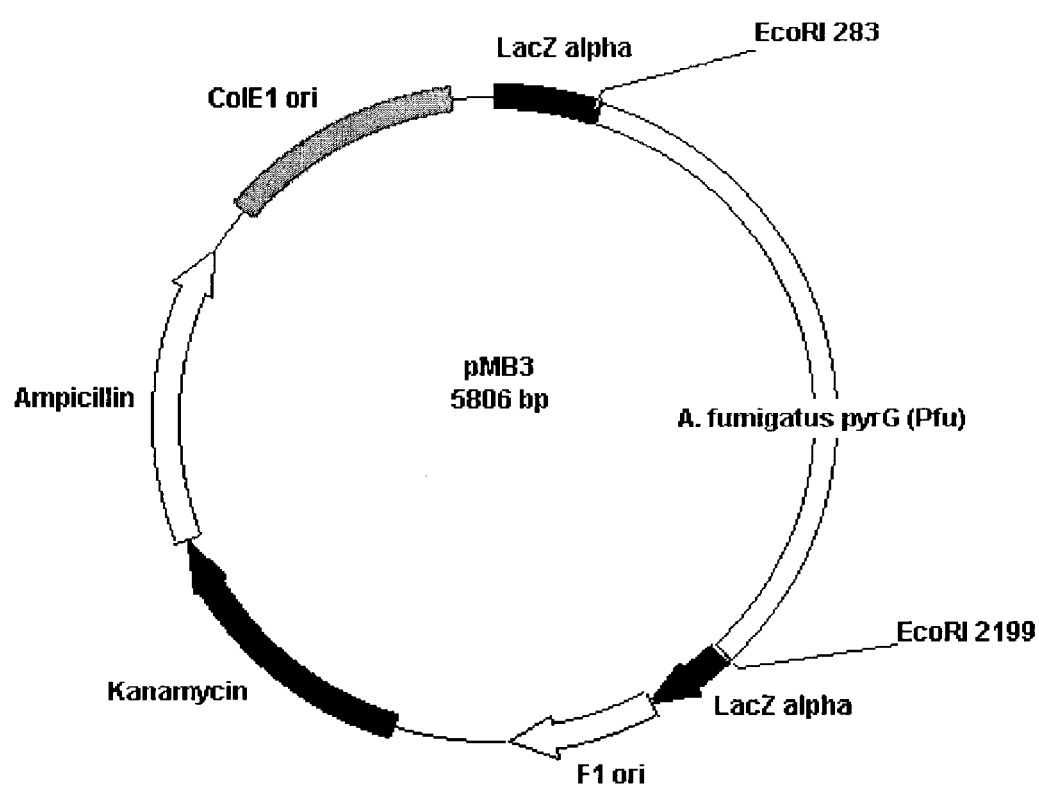

FIGURE 12. Identification of mutated gene in strain MA205

BLASTX search identifies two yeast proteins as nearest matches:

```
                                                             Score        E
Sequences producing significant alignments:                  (bits)    Value sp|P38805|YHO8_YEAST  HYPOTHETICAL 35.1 KD PROTEIN IN NAM8-GAR1 ...    194    5e-49
sp|O14180|YDS4_SCHPO  HYPOTHETICAL 35.8 KD PROTEIN C4F8.04 IN CH...    173    1e-42
gi|3695379   (AF096370) contains similarity to a C. elegans hypot...   143    8e-34
emb|CAA93858|   (Z70034) similarity to 35.1KD hypothetical yeast ...   113    1e-24
gb|AAD14602|    (AF092910) stage specific peptide 24 [Trypanosoma ...   81    8e-15
emb|CAB11643|   (Z98974) hypothetical protein [Schizosaccharomyce...    76    2e-13
emb|CAB05841|   (Z83246) predicted using Genefinder; cDNA EST EMB...    75    4e-13
sp|P53941|YNH5_YEAST  HYPOTHETICAL 33.5 KD PROTEIN IN MKS1-MSK1 ...     74    8e-13
emb|CAB11063|   (Z98531) hypothetical protein [Schizosaccharomyce...    33    1.7
gi|2650581   (AE001102) ATP-dependent RNA helicase, putative [Arc...    33    2.2
emb|CAA74646|   (Y14274) putative serine/threonine protein kinase...    32    4.9 sp|P38805|YHO8_YEAST HYPOTHETICAL 35.1 KD PROTEIN IN NAM8-GAR1 INTERGENIC REGION
         >gi|626640|pir||S46718 hypothetical protein YHR088w -
         yeast (Saccharomyces cerevisiae) >gi|487932 (U00060)
         Yhr088wp [Saccharomyces cerevisiae]
         Length = 295

Score =  194 bits (488), Expect = 5e-49
 Identities = 97/234 (41%), Positives = 146/234 (61%), Gaps = 29/234 (12%)
```

FIGURE 13. Southern Blot showing random integration events

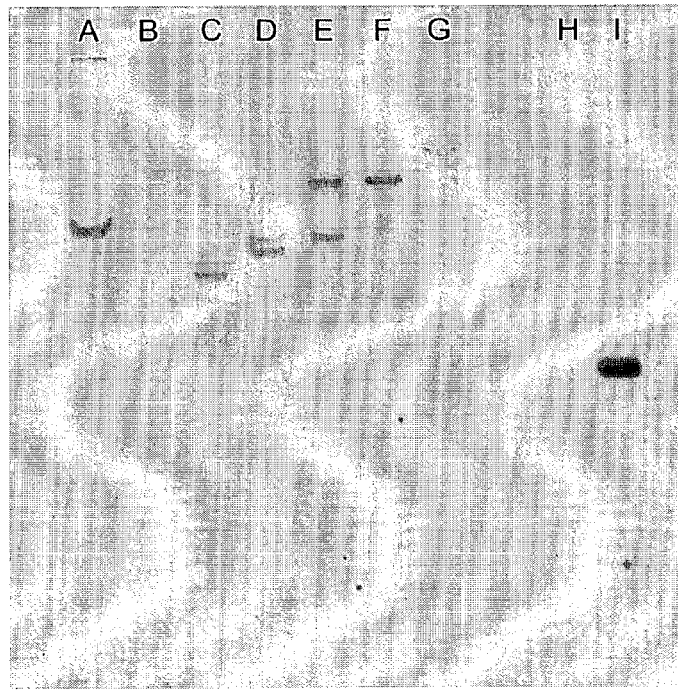

Genomic DNA digested with EcoRI. Probe was pUC18 labelled using the DIG method.

Lane
- A. Single integration. Uncut ppyrG plasmid. Electroporation of conidia. AF293 haploid *pyrG*⁻ strain.
- B. Single integration. Uncut ppyrG plasmid. Electroporation of conidia. AF293 haploid *pyrG*⁻ strain.
- C. Double integration. Uncut ppyrG plasmid. Electroporation of conidia. AF293 haploid *pyrG*⁻ strain.
- D. Double integration. Uncut ppyrG plasmid. Electroporation of conidia. AF293 haploid *pyrG*⁻ strain.
- E. Double integration. Uncut ppyrG plasmid. Electroporation of conidia. AF293 haploid *pyrG*⁻ strain.
- F. Single integration. Uncut ppyrG plasmid. Electroporation of conidia. AF293 haploid *pyrG*⁻ strain.
- G. Single integration. XbaI cut ppyrG plasmid. Protoplast transformation. AF293 diploid *pyrG*⁻/ *pyrG*⁻/*niaD*⁻/*cnx*⁻ strain.
- H. Negative control
- I. Positive control

SEQUENCE LISTING

```
<160> NUMBER OF SEQ ID NOS: 27

<210> SEQ ID NO 1
<211> LENGTH: 20
<212> TYPE: DNA
<213> ORGANISM: Escherichia coli

<400> SEQUENCE: 1
cgatgtagga gggcgtggat                                               20

<210> SEQ ID NO 2
<211> LENGTH: 20
<212> TYPE: DNA
<213> ORGANISM: Escherichia coli

<400> SEQUENCE: 2
atcgcctcgc tccagtcaat                                               20

<210> SEQ ID NO 3
<211> LENGTH: 20
<212> TYPE: DNA
```

<213> ORGANISM: Escherichia coli

<400> SEQUENCE: 3
cttagccaga cgagcgggtt                                              20

<210> SEQ ID NO 4
<211> LENGTH: 20
<212> TYPE: DNA
<213> ORGANISM: Escherichia coli

<400> SEQUENCE: 4
caagacctgc ctgaaaccga                                              20

<210> SEQ ID NO 5
<211> LENGTH: 20
<212> TYPE: DNA
<213> ORGANISM: Escherichia coli

<400> SEQUENCE: 5
tcgtccatca cagtttgcca                                              20

<210> SEQ ID NO 6
<211> LENGTH: 23
<212> TYPE: DNA
<213> ORGANISM: Escherichia coli

<400> SEQUENCE: 6
tcccgctcag aagaactcgt caa                                          23

<210> SEQ ID NO 7
<211> LENGTH: 23
<212> TYPE: DNA
<213> ORGANISM: Escherichia coli

<400> SEQUENCE: 7
ttgggtggag aggctattcg gct                                          23

<210> SEQ ID NO 8
<211> LENGTH: 23
<212> TYPE: DNA
<213> ORGANISM: Escherichia coli

<400> SEQUENCE: 8
tgttgtgccc agtcatagcc gaa                                          23

<210> SEQ ID NO 9
<211> LENGTH: 23
<212> TYPE: DNA
<213> ORGANISM: Escherichia coli

<400> SEQUENCE: 9
agccgaatag cctctccacc caa                                          23

<210> SEQ ID NO 10
<211> LENGTH: 23
<212> TYPE: DNA
<213> ORGANISM: Agrobacterium tumefaciens

<400> SEQUENCE: 10
cagattattt ggattgagag tga                                          23

<210> SEQ ID NO 11
<211> LENGTH: 15

```
<212> TYPE: DNA
<213> ORGANISM: arbitrary degenerate
<220> FEATURE:
<221> NAME/KEY: misc_feature
<222> LOCATION: (1)..(1)
<223> OTHER INFORMATION: a, g, c or t
<220> FEATURE:
<221> NAME/KEY: misc_feature
<222> LOCATION: (6)..(6)
<223> OTHER INFORMATION: g or c
<220> FEATURE:
<221> NAME/KEY: misc_feature
<222> LOCATION: (8)..(8)
<223> OTHER INFORMATION: a or t
<220> FEATURE:
<221> NAME/KEY: misc_feature
<222> LOCATION: (10)..(10)
<223> OTHER INFORMATION: g or c
<220> FEATURE:
<221> NAME/KEY: misc_feature
<222> LOCATION: (12)..(12)
<223> OTHER INFORMATION: a or t

<400> SEQUENCE: 11
ntcgantntn gngtt                                                   15

<210> SEQ ID NO 12
<211> LENGTH: 16
<212> TYPE: DNA
<213> ORGANISM: arbitrary degenerate
<220> FEATURE:
<221> NAME/KEY: misc_feature
<222> LOCATION: (1)..(1)
<223> OTHER INFORMATION: a, g, c or t
<220> FEATURE:
<221> NAME/KEY: misc_feature
<222> LOCATION: (7)..(7)
<223> OTHER INFORMATION: g or c
<220> FEATURE:
<221> NAME/KEY: misc_feature
<222> LOCATION: (8)..(8)
<223> OTHER INFORMATION: a or t
<220> FEATURE:
<221> NAME/KEY: misc_feature
<222> LOCATION: (11)..(11)
<223> OTHER INFORMATION: a, g, c or t
<220> FEATURE:
<221> NAME/KEY: misc_feature
<222> LOCATION: (13)..(13)
<223> OTHER INFORMATION: a or t

<400> SEQUENCE: 12
ngtcgannga nangaa                                                  16

<210> SEQ ID NO 13
<211> LENGTH: 16
<212> TYPE: DNA
<213> ORGANISM: arbitrary degenerate
<220> FEATURE:
<221> NAME/KEY: misc_feature
<222> LOCATION: (1)..(1)
<223> OTHER INFORMATION: a or t
<220> FEATURE:
<221> NAME/KEY: misc_feature
<222> LOCATION: (5)..(5)
<223> OTHER INFORMATION: a, g, c or t
<220> FEATURE:
<221> NAME/KEY: misc_feature
<222> LOCATION: (8)..(8)
<223> OTHER INFORMATION: a or t
<220> FEATURE:
<221> NAME/KEY: misc_feature
<222> LOCATION: (10)..(10)
<223> OTHER INFORMATION: a, g, c or t
<220> FEATURE:
```

```
<221> NAME/KEY: misc_feature
<222> LOCATION: (13)..(13)
<223> OTHER INFORMATION: a, g, c or t

<400> SEQUENCE: 13
ngtgnagnan canaga                                                    16

<210> SEQ ID NO 14
<211> LENGTH: 17
<212> TYPE: DNA
<213> ORGANISM: Aspergillus fumigatus

<400> SEQUENCE: 14
gtttgaggcg aattctc                                                   17

<210> SEQ ID NO 15
<211> LENGTH: 18
<212> TYPE: DNA
<213> ORGANISM: Aspergillus fumigatus

<400> SEQUENCE: 15
ctctcagaca gaattcgt                                                  18

<210> SEQ ID NO 16
<211> LENGTH: 16
<212> TYPE: DNA
<213> ORGANISM: Escherichia coli

<400> SEQUENCE: 16
atccatcaca ctggcg                                                    16

<210> SEQ ID NO 17
<211> LENGTH: 20
<212> TYPE: DNA
<213> ORGANISM: Escherichia coli

<400> SEQUENCE: 17
taatacgact cactataggg                                                20

<210> SEQ ID NO 18
<211> LENGTH: 16
<212> TYPE: DNA
<213> ORGANISM: Escherichia coli

<400> SEQUENCE: 18
gtaaaacgac ggccag                                                    16

<210> SEQ ID NO 19
<211> LENGTH: 17
<212> TYPE: DNA
<213> ORGANISM: Escherichia coli

<400> SEQUENCE: 19
gttttcccag tcacgac                                                   17

<210> SEQ ID NO 20
<211> LENGTH: 20
<212> TYPE: DNA
<213> ORGANISM: Escherichia coli

<400> SEQUENCE: 20
gcagagcgag gtatgtaggc                                                20
```

```
<210> SEQ ID NO 21
<211> LENGTH: 20
<212> TYPE: DNA
<213> ORGANISM: Escherichia coli

<400> SEQUENCE: 21
aagccctccc gtatcgtagt                                                  20

<210> SEQ ID NO 22
<211> LENGTH: 20
<212> TYPE: DNA
<213> ORGANISM: Escherichia coli

<400> SEQUENCE: 22
atacctgtcc gcctttctcc                                                  20

<210> SEQ ID NO 23
<211> LENGTH: 18
<212> TYPE: DNA
<213> ORGANISM: Escherichia coli

<400> SEQUENCE: 23
tttatccgcc tccatcca                                                    18

<210> SEQ ID NO 24
<211> LENGTH: 20
<212> TYPE: DNA
<213> ORGANISM: Escherichia coli

<400> SEQUENCE: 24
gccttcctgt ttttgctcac                                                  20

<210> SEQ ID NO 25
<211> LENGTH: 24
<212> TYPE: DNA
<213> ORGANISM: Aspergillus fumigatus

<400> SEQUENCE: 25
ctacctcgag aattcgcctc aaac                                             24

<210> SEQ ID NO 26
<211> LENGTH: 22
<212> TYPE: DNA
<213> ORGANISM: Aspergillus fumigatus

<400> SEQUENCE: 26
ggcgacgaat tctgtctgag ag                                               22

<210> SEQ ID NO 27
<211> LENGTH: 1060
<212> TYPE: DNA
<213> ORGANISM: Aspergillus fumigatus

<400> SEQUENCE: 27
ctcgaggtcg acggtatcga taagcttgat tagccgaata gctctccacc caaaatcctc      60
ttcaccacct cgctcaactc taccctccat aacgaggcca gatcccctac cgatctgttt     120
cctaacagcg tttatatccg tcgtacggcc catcgctatt cccacaagtt ctccatccgc     180
gagattgctg ccttcgcgtc gaatcggaac tataccagcg tcgtggttct ccaggaggat     240
cagaaacgac cttccggtct gacgatcgtc cacctacctc aggtctcac cttccatttt     300 actattagca gatggataga aggcaagaag cttccgggac atggaaatgc caccgagcac     360
```

-continued

```
cggccggaac taatcctcaa caacttccgg actcctcctg gtctacttac ggcccatctc    420
ttccggagca tgttcccacc acaaccggac ctagaaggac gtcaagttgt cgcaattcac    480
aaccaaagag actacctatt tctccggcgt catcgttatg tgttccgtga gaagcgcgag    540
actgaaaaga gtgtcgttgg tacagacggc aaagagatca agggtgtgga aggcattcgc    600
gccggccttc aagagcttgg tcccgcaata aacttcaagc tgcggcgagt tgacaaagga    660
attcagcgtg ctagcggaca ggagtgggag tggaaaggag gcatggaaaa acagcgtact    720
aagttccagc tgtagcatgc tctcatcccc ttttatacct tttgttatgt gtctgattgc    780
atcattgggt ttgcatggag tttagctttc aagaatgggt ctttgatgg cttttcacg     840 tgcggttata gtttcttcat gactgtccag atccttatac catctgtaga taatgtactg    900
aaaaccacta ttctatcaaa gtggtgtttg ggccaaatgg tggcatctca tctactctca    960
aatgcacaca tgcgattgat caatagataa gatgctcaaa tacaacaatc tgtaatccat   1020
gttttgattc ccgggggta cccgaaatcg aattcctgca                          1060
```

MUTANT BANK

The present invention relates to the generation of mutant banks of micro-organisms comprising a population of mutant cells in which essentially every gene within the genome is inactivated and uses thereof.

Due to the advances made by various genome sequencing projects, the art has reached the position that many genes have now been cloned and sequenced. However, a problem remains that for most identified genes a link has not been made with function (i.e. how an identified gene may effect phenotype).

One way by which gene function may be identified is to compare the phenotypes of mutant cells or organisms with the known phenotype of a "wild-type" cell or organism. The gene responsible for this phenotypic change may be identified by DNA sequencing of mutant and wild-type cells. The identity of the gene product may then be easily established. Such knowledge can give rise to industrially useful processes in which the activity of the gene, or its product, is modulated to achieve specific goals. For instance, identification of a mutation that reduces the growth of a pathogenic mould provides valuable information for developing therapeutic strategies.

Various strategies have been proposed for identifying mutations in specific organisms. For instance, an insertional mutation technique for plants is disclosed in WO 99/14373. This document discloses a means of selecting and identifying insertional mutations in a population of plant cells based upon a method utilising the Ti plasmid of *Agrobacterium tumefaciens* (a gram-negative soil bacterium) for effecting transformation.

EP-A-0 870 835 also relates to the use of the Ti plasmid of *Agrobacterium*. It discloses that the abovementioned Ti plasmid technique may also be used to transform moulds from the fungal subdivisions Ascomycotina, Basidiomycotina, Deuteromycotina, Mastigomycotina and Zygomycotina.

One of the problems associated with the mutant populations disclosed by the prior art is that often no account is taken of the effect of lethal mutations. A lethal mutation results in the death of particular individuals and therefore any mutant population generated according to such prior art techniques would result in an "incomplete" population comprising "non-lethal" mutants. It is an aim of the present invention to obviate or mitigate this disadvantage, as well as others, associated with the prior art.

According to a first aspect of the present invention there is provided a mutant bank of micro-organisms comprising a population of mutant cells in which at least one cell has a mutation that disrupts the activity of at least one gene, said micro-organisms being diploid and being inducible into haploid form.

The micro-organisms may normally occur in a haploid form and are, preferably, first induced into the diploid form.

Preferably, a plurality of cells in the population each individually have a mutation which disrupts the activity of at least one gene, so that, preferably, collectively the said plurality of cells have mutations in a plurality of genes within the genome.

Preferably, the said plurality of genes makes up 0.001% of the genes within the genome, more preferably 0.01%, most preferably 0.1%, even more preferably, 10%, even more especially substantially all the essential genes and most especially all the genes of the genome of the micro-organism.

According to a second aspect of the present invention there is provided a method of generating a mutant bank of micro-organisms comprising a population of mutant cells in which at least one cell has a mutation that disrupts the activity of at least one gene, said method comprising the steps of:

(i) culturing a population of micro-organisms; and (ii) inducing a mutation in at least one cell of the population which mutation disrupts the activity of at least one gene in the genome of the micro-organism, said micro-organisms being diploid and being inducible into haploid form.

Preferably, the method comprises the further step of exposing the diploid micro-organisms to an agent that induces the micro-organisms into haploid form after generating the mutant bank.

Preferably, the method comprises the further step of separating and culturing the haploid micro-organisms as single clones after the induction of the micro-organisms into haploid form.

Preferably, the method comprises the further step of selecting clones for which the chosen phenotype is altered relative to a wild type micro-organism after separating and culturing the haploid micro-organisms.

Preferably, the method comprises the further step of identifying the mutated gene in each of the selected clones after selecting clones for which the chosen phenotype is altered relative to a wild type micro-organism.

The micro-organisms may normally occur in a haploid form. Therefore, preferably, the method of the second aspect further includes the step of first inducing the haploid into diploid form prior to culturing the said population.

According to a third aspect of the present invention there is provided a method of identifying genes in a micro-organism which contribute to a chosen phenotype comprising:

(i) generating a mutant bank of diploid micro-organisms consisting of a population of mutant cells in which at least one cell has a mutation which disrupts the activity of at least one gene;

(ii) exposing the diploid micro-organisms to an agent that induces the micro-organisms into haploid form;

(iii) separating and culturing the haploid micro-organisms as single clones; and (iv) selecting clones for which the chosen phenotype is altered relative to a wild type micro-organism; and (v) identifying the mutated gene in each of the selected clones.

According to a fourth aspect of the present invention there is provided a mutant bank of diploid micro-organisms consisting of a population of mutant cells in which each individual cell has a mutation that disrupts the activity of one gene, said population collectively having a mutation in every gene within the genome and wherein the mutant bank may be induced into haploid form.

According to a fifth aspect of the present invention there is provided a method of identifying genes in a micro-organism which contribute to a chosen phenotype comprising:

(i) generating a mutant bank of diploid micro-organisms consisting of a population of mutant cells in which each individual cell has a mutation which disrupts the activity of one gene, said population collectively having a mutation in every gene within the genome;

(ii) exposing the diploid micro-organisms to an agent that induces the micro-organisms into haploid form;

(iii) separating and culturing the haploid micro-organisms as single clones; and (iv) selecting clones for which the chosen phenotype is altered relative to a wild type micro-organism; and (v) identifying the mutated gene in each of the selected clones.

By "disrupts the activity of one gene" we mean that the gene contains a mutation that prevents transcription or translation of the protein encoded by the gene.

Alternatively, the translated protein has no activity, or at least altered activity, relative to the wild type gene product that results in a measurable phenotypic change.

The mutant banks may be used according to the present invention to screen the genome of the micro-organism for genes that are linked with a specific phenotype. This knowledge may be used to develop modulators of the gene and may lead to the development of new medicaments, pesticides, disinfectants etc. which may be targeted against the micro-organism.

The prior art does not contemplate mutant banks of micro-organisms comprising a population of mutant cells in which essentially the activity of every gene within the genome is disrupted and which may be converted between diploid and haploid forms.

One of the advantages of the mutant banks according to the invention is that a complete diploid population may be cultured under suitable conditions. This is possible because the wild type copy of the gene will rescue any individual that may otherwise grow poorly, or even not be viable, should the mutant copy of the gene predominate. Thus, the diploid mutant bank may comprise a population of mutant, viable cells in which essentially the activity of every gene within the genome is disrupted rather than an "incomplete" population comprising "non-lethal" mutants.

Furthermore, the mutant bank may be comprised within a population of cells which also comprises cells in which no mutations may have occurred and/or in which more than one mutation may have occurred.

When the diploid mutant bank is induced into haploid form (step (ii)) of the third and fifth aspects any phenotypic changes in the haploid mutants may be interpreted by a technician to provide valuable information about gene function. For instance, the haploid cells may be grown under normal culture conditions. Under these circumstances, the death of a haploid clone would imply that the mutation caused a lethal phenotypic change. The clone could then be isolated from the original diploid sample and the mutant gene identified.

When organisms are used which are naturally found as haploids, it is preferred that the method of the third and fifth aspects of the invention comprises an initial step of converting the haploid cells into diploid form before mutations are induced as defined by step (i) of the method of the third and fifth aspects of the invention.

Organisms which are normally haploid, may be induced into diploid form utilising the methods described in the Examples at 1.4 and 1.5.

It is preferred that the mutant banks are used according to the invention to screen the genome of a micro-organism for genes which contribute to a chosen phenotype by growing the micro-organisms in permissive or selective growth media. The choice of permissive or selective growth media will depend upon the phenotype of interest. For instance, the haploid cells may be initially grown in a media which is osmotically buffered such that cells with weak cell walls (which would lyse in a normal media) are able to survive. Clones which survive under such circumstances, and which do not when grown in normal media, may be selected. The mutant genes, (and thereby the gene products), in the selected clones may be identified by conventional molecular biology techniques. The identification of such gene products may be used as an aid for rationally identifying gene products which regulate osmoregulation and could also identify leads for developing anti-microbial agents that will induce cell lysis by disrupting osmoregulation.

Mutant banks used according to the invention are particularly useful for identifying new anti-microbial drug targets. By a "drug target" we mean the site of action of a drug.

By identifying essential genes in the mutant banks and then analyzing them (e.g. using computer analysis—bioinformatics), the commonality of the gene in other micro-organisms (or fungi) can be established and any significant differences between mammals (e.g. man or mouse) and the micro-organism defined. For instance, a good antifungal drug target would be a protein encoded by a gene which is shared by all fungi (and be very similar between different species) and not found in man at all. By a continuous process of identifying possible new targets, on the basis that an identified mutant gene had an effect on phenotype, and then bioinformatic analysis to rule candidates out, multiple new targets may be identified in a short time-frame.

The mutant banks also provide a simple means of establishing the mechanism of action of a compound known to have anti-fungal activity. Colonies from the banks may be plated out on media containing the anti-fungal compound of interest and resistant or less susceptible colonies examined to determine which gene has been inactivated by insertional mutagenesis. This gene product is the likely target for that anti-fungal agent. This represents a rapid and simple means for determining the mechanism-of-action of the agent.

In addition to identifying and validating anti-fungal targets, other special characteristics can be selected for. For instance, the transporter genes that mediate drug resistance may be identified according to the method of the invention. There are about 30 transporter genes in yeast but only 3 have been found in *Aspergillus fumigatus* to date. In fungi the most common resistance mechanism is due to the active export of potentially lethal drugs from within the fungal cell. Transport mutants may be identified by selecting from the haploid mutant bank for drug sensitive strains (indicating that a transporter gene is non-functional). Drug sensitive mutants (i.e. incapable of drug export) will make good strains for drug development because the potential for future resistance by these efflux mechanisms can be directly assessed.

The micro-organism may be a yeast or any fungus, preferably, a filamentous fungus which may be switched between diploid and haploid form.

A most preferred micro-organism is *A. fumigatus* and related strains. *A. fumigatus* is a haploid organism and the most common human mould pathogen. The genome of *A. fumigatus* is thought to comprise 8,000-11,000 genes. It is important when developing anti-microbial agents to select a suitable target which will not only kill the micro-organism but which are also selective. In this respect it is expected that approximately 750-1000 genes in *A. fumigatus* will be essential and therefore potential targets. Of the essential genes possibly a quarter will be new genes with no known counterpart in yeast-fungi, over 100 are likely to be structural genes (which do not make good targets) and as many as 500 will be common to man. This leaves an estimated 150 candidate targets which may encode proteins that could represent leads for developing anti-microbial agents. The method of the second aspect of the invention may be used to identify candidate clones. Further screening of the candidates may be achieved by employing bioinformatics and it is estimated that such an approach will generate 15-25 validated targets. Some may be shared by bacteria, raising the possibility of finding anti-microbials that have both antibacterial and antifungal activity.

*A. fumigatus* clinical isolates AF300 and AF293 (available to the public from the NCPF repository (Bristol, U.K.) and the CBS repository (Belgium)) are preferred strains which may be formed into mutant banks according to the present invention.

Another preferred micro-organism is *Candida glabrata*. Candida species are important yeast fungal pathogens of humans. Until recently, *C. glabrata* was considered a relatively non-pathogenic commensal fungal organism of human mucosal tissues. However, with the increased use of immunosuppressive agents, mucosal and systemic infections caused by *C. glabrata* have increased significantly, especially in the human population infected with HIV. *C. glabrata* currently ranks second or third as the causative agent of superficial (oral, oesophageal, vaginal, or urinary) or systemic candidal infections. A number of factors have been proposed as being important to virulence but details of the host-pathogen interaction are, however, largely unknown. A major obstacle in *C. glabrata* infections is their innate resistance to azole antimycotic therapy, which is very effective in treating infections caused by other *Candida* species. *C. glabrata*, formerly known as *Torulopsis glabrata*, contrasts with other *Candida* species in its nondimorphic blastoconidial morphology and haploid genome. We have realised that the possession of a haploid genome is a useful feature in the production of mutant banks as most Candida species are obligate diploids with no known haploid forms and therefore *C. glabrata* is a preferred micro-organism which may be made into a mutant bank according to the invention.

*A. fumigatus* and *C. glabrata* normally have only one set of chromosomes (haploid) and conventionally would not be considered for the formation of a bank of mutants because lethal gene knockouts would not survive and therefore the bank would be incomplete. However, the inventors have appreciated that these moulds can be induced to carry a double set (diploid) of genes. They therefore realised that this property could be exploited such that a stock mutant bank may be maintained in diploid form. One gene from each pair should be in wild type form and thereby allow the organisms to be phenotypically normal. When desired the cells may be allowed to return to haploid form and the effects of the mutant gene identified.

It will be appreciated that the method of the invention used in *A. fumigatus* may be usefully employed to gain knowledge relating to homologous genes for other species of micro-organism. For instance, biotechnology companies are interested in improving strains of filamentous fungi which are used extensively in industry for the production of soy sauce, citric acid etc. Furthermore, the production of mutant banks or knowledge gained from the *Aspergillus* mutant bank in plant pathogenic fungi is useful to the agrochemical industry for the development of broad-specificity anti-fungal drugs.

Preferably, the mutant banks comprise a population of cells in which the mutations have been randomly induced. Preferably, there has been a random knock out of essentially all genes in the micro-organism.

The mutant banks may be generated (according to step (i) of the third and fifth aspects of the invention) by exposing a population of micro-organisms to an agent which randomly causes single mutations in each individual micro-organism. It is preferred that the mutant bank is formed by an insertional mutagenesis method. Preferably, a DNA molecule is inserted into each gene to cause the mutation. The DNA molecule may be a selectable marker which is, preferably, a pyrG gene, more preferably, the pyrG gene from *A. fumigatus*.

Advantageously, the pyrG gene is a preferred selectable marker because it may be very tightly regulated since there is an absolute requirement of pyrG mutants for uridine and uracil supplementation in the growth medium. Advantageously, this substantially reduces the number of false negatives.

Preferably, the pyrG gene is harboured on a plasmid which is, preferably, an *Aspergillus* pyrG containing plasmid.

The micro-organism may be a fungus, preferably, a filamentous fungus and, most preferably, *A. fumigatus*. In a preferred embodiment the micro-organism is AF300 or AF293.

Alternatively, the micro-organism may be a yeast, preferably, *C. glabrata*.

Preferably, the mutations have been randomly induced, more preferably, by an insertional mutagenesis method. Preferably, a DNA molecule is inserted into each gene to cause the mutation. The DNA molecule may be a selectable marker which is, preferably, a pyrG gene, more preferably, the pyrG gene from *A. fumigatus*. Preferably, the pyrG gene is harboured on a plasmid which is, preferably, an *Aspergillus* pyrG containing plasmid.

Examples of the pyrG containing plasmid are shown in FIGS. 6, 7, 10 and 11.

Preferably, the plasmid is introduced into the micro-organism by electroporation (see section 1.7.1).

Preferably, the diploid micro-organism is a mutant for the pyrG$^-$ phenotype.

Advantageously, this allows for the selection of the pyrG gene containing plasmids.

Preferably, the diploid mutant micro-organism is generated using the following steps:

(i) isolating a first haploid mutant comprising a first auxotrophic marker wherein the first auxotrophic marker results in the pyrG$^-$ phenotype;

(ii) isolating a second haploid mutant using the first haploid mutant isolated in step (i), said second mutant comprising the first pyrG$^-$ auxotrophic marker and a second auxotrophic marker;

(iii) isolating a third haploid mutant using the first haploid mutant isolated in step (i), said third mutant comprising the first pyrG$^-$ auxotrophic marker and a third auxotrophic marker; and (iv) mating the second and third haploid mutants isolated in steps (ii) and (iii) to generate the diploid mutant exhibiting the pyrG phenotype.

Preferably, the second and third auxotrophic markers are selected from niaD$^-$ or cnx$^-$. Preferably, cells which are unable to utilise nitrate alone were classified as niaD$^-$ mutants and, preferably, mutants unable to utilise mitrate or hypoxanthine were classified as cnx$^-$ mutants.

Preferably, the mutant diploid micro-organism is a double mutant for the pyrG⁻ phenotype, i.e. pyrG⁻/pyrG⁻ phenotype. Preferably, the double mutants (pyrG⁻/pyrG⁻ phenotype) were made using a haploid single pyrG⁻ mutant as a parental strain.

Preferably, the order of making the diploid double mutants was found to be important since starting with a niaD⁻ or cnx⁻ mutant as the parental strain we were unable to then isolate a niaD⁻/pyrG⁻ or cnx⁻/pyrG⁻ mutant.

Preferably, the method comprises use of the Frontier method (section: 1.4.1) for the production of diploid micro-organisms in *A. fumigatus*.

Preferably, the haploid mutants are incubated at a temperature in the range of 20-36° C., more preferably, in the range of 24-33° C. and, most preferably, in the range of 26-30° C. Most preferably, the haploid mutants are incubated at 28° C.

Advantageously, incubation at a lower temperature slows down growth of the haploid mutants thereby increasing the chance of heterokaryon formation and the subsequent production of diploid mutants with which to make the mutant bank. Preferably, putative mutant cell transformants are identified using a microscope when they are substantially not visible to the naked eye at the earliest stage possible in their development. Preferably, putative mutant cell transformants are identified at 32 to 48 hours in to their development, more preferably, at 34 to 46 hours and, most preferably, at 36 to 44 hours in to their development.

Preferably, the minimum feasible time that putative mutant cell transformants could be identified using a microscope is 36-48 hrs. Most methods rely on the macroscopic identification of colonies, i.e. by eye when they have reached a particular size. By this time, many of the colonies are sporulating which poses a cross-contamination problem with other nearby putative transformants. More importantly, due to the randomness of the transformation procedure, there will be a whole range of transformants which are affected to a greater or lesser degree in their growth rates. Some of these transformants may never reach macroscopic size and would hence be lost from the population of the mutant bank as a whole. Identification of these transformants by microscope at an early stage allows them to be transferred to a richer, more complete medium where they have a better chance to grow to a size where DNA can be extracted and the genetic mutation identified.

According to a still further aspect of the present invention there is provided SEQ ID No. 27 and homologues thereof, preferably, functional and/or structural homologues thereof.

SEQ ID No. 27 (see sequence listing) may be used for the manufacture of a medicament for treatment of an infection of *A. fumigatus*.

In an alternative emodiment, the insertional mutagenesis may be carried out using the Ti plasmid. The use of the Ti plasmid in filamentous fungi has previously been described (de Groot et al. (1998) Nature Biotechnology 16:839-842), but it has not been used for the generation of mutant banks according to the first aspect of the invention nor has it been used in filamentous fungi such as *A. fumigatus* or in *C. glabrata*.

The Ti plasmid transformation methods disclosed in EP-A-0 870 835 (incorporated herein by reference) may be used, and adapted as appropriate, to generate mutant banks according to the invention. According to one embodiment (see the example), the physical steps of transforming diploid *A. fumigatus* may be essentially the same as those disclosed in EP-A-0 870 835.

The mutant bank may be generated by transformation with a Ti plasmid vector based on the binary vector pBIN19 (disclosed in: Bevan. (1984) Nucleic Acids Research 22: 8711-8721).

It is most preferred that LBA4404 and GV3101 strains of *A. tumefaciens* (identified in Table 1) are used to generate the mutant banks of the present invention.

TABLE 1

| Strain | Genotype | Reference disclosing strain |
|---|---|---|
| LBA 4404 | Ach5 Rif ʳ containing plasmid pAL4404 (ΔT_L, ΔT_R, Δtra, Δocc) a deletion of pTiAch5. | Oooms et al. (1981) Gene 14: 33-50. |
| GV3101 | C58C1 Rif ʳ containing plasmid pMP90 (Gm ʳ) a deletion of pTiC58. | Koncz & Schell, (1986) Molecular and General Genetics 204: 383-396. |

Most preferred transformation steps are described in 1.7 of the Example.

Following generation of the diploid mutant bank, the cells are induced into haploid form according to step (ii) of the method of the invention. A preferred technique for inducing the cells into haploid form is described in the Example under 1.6.

The haploid cells from step (ii) are then separated and cultured according to step (iii). This may be achieved by conventional dilution and spread plating of the culture and is also described at 1.6 of the Example.

Clones with an altered phenotype (step (iv)) may be isolated by a variety of conventional means (e.g. by growth on a selective medium).

Once clones have been selected according to step (iv) of the method of the invention it is preferred that the mutated gene is identified. Identification of the mutated gene may be achieved by including sections of marker DNA during the generation of the mutant bank. For instance, a gene may be insertionally inactivated by incorporating a marker DNA sequence which may be later identified using conventional molecular biology techniques (e.g. using labelled probes for the marker).

Alternatively, the marker may be used as a target for a primer which can be used to directly sequence and amplify the mutant gene. This approach has several advantages over known mutational techniques. For instance:

(1) it is not necessary to have discovered the gene previously;

(2) the essential function of the gene is established concurrently with its identification; and (3) it is extremely rapid.

Various methods known to those skilled in the art may be used to identify the gene. Preferred methods are outlined at 1.9 and 1.10 of the methods section of the Example.

All of the features described herein may be combined with any of the above aspects, in any combination.

An embodiment of the present invention will now be described, by way of example, with reference to the accompanying drawings in which:

FIG. 1 is a schematic representation of plasmid pAN7-1;
FIG. 2 is a schematic representation of plasmid pRok2;
FIG. 3 is a schematic representation of plasmid pRic1;
FIG. 4 is a schematic representation of plasmid pUC 18;
FIG. 5 is a schematic representation of plasmid pRic2;
FIG. 6 is a schematic representation of plasmid pRic3;
FIG. 7 is a schematic representation of plasmid ppyrG;
FIG. 8 is a schematic representation of plasmid pCR2.1;

FIG. 9 is a schematic representation of plasmid pTT;

FIG. 10 is a schematic representation of plasmid pMB2;

FIG. 11 is a schematic representation of plasmid pMB3;

FIG. 12 is a BLASTX search result used for the identification of mutated gene in strain MA205;

FIG. 13 is a Southern blot showing integration events; and

To the Sequence Listing.

EXAMPLE

1. Methods 1.1 Bacterial and Fungal Strains:

For bacterial cloning the *E. coli* strain Top10 (F−, mcrA Δ (mrr-hsdRMS-mcrBC) φ80lacZΔM15 ΔlacX74 deoR recA1 araD139 Δ(ara-leu)7697 galU galK rpsL(Str$^R$) endA1 nupG) was used.

The *A. tumefaciens* strains LBA4404 and GV3101 (see Table 1) were used for the transformation of *A. fumigatus*.

*A. fumigatus* clinical isolates AF300 and AF293 (available to the public from the NCPF repository (Bristol, U.K.); the CBS repository (Belgium) or from Dr. David Denning clinical isolate culture collection, Hope Hospital, Salford. U.K.) are preferred strains which may be formed into mutant banks according to the present invention.

AF300: Isolated 1995. Royal Manchester Children's Hospital. Leukaemia patient.

AF293: Isolated 1993. Donated by Shrewsbury PHLS. Lung biopsy, invasive aspergillosis with aplastic anaemia.

1.2 Plasmid Construction:

1.2.1 Plasmid pRic1

Plasmid pRic1 (see FIG. 3) was constructed by cloning a 4 kb HindIII-BglII fragment, which is present on the vector pAN7-1 (Punt et al. (1987) Gene 56: 117-124; see FIG. 1) and contains the promoter from the *Aspergillus nidulans* gpd gene fused to the coding region of the *E. coli* hygromycin B phosphotransferase (hph) gene and followed by terminator sequences from the *A. nidulans* trpC gene, into the HindIII-BamHI site of the Cauliflower Mosaic Virus (CaMV) 35s promoter region of the binary vector pRok2 (a derivative of the binary vector pBin19) pRok2 is disclosed in: Baulcombe et al. (1986) Nature 321: 446-449; and FIG. 2).

1.2.2 Plasmid pRic2

Plasmid pRic2 (see FIG. 5) was constructed by cloning the entire pUC18 plasmid (see: Yanisch-Perron et al (1985) Gene 33: 103-119; and FIG. 4) linearised with HindIII into the HindIII site of pRic1.

1.2.3. Plasmid pRic3

Plasmid pRic 3 (see FIG. 6) was constructed by cloning the entire ppyrG plasmid (Fungal Genetics Stock Centre, and FIG. 7) linearised with XbaI into the XbaI site of pRok2.

The *A. tumefaciens* strain GV3101 was electroporated with the constructs pRic1, pRic2 and pRic3 using a Biorad Genepulser (2.5 kV, 600 Ω, 25° F.). The constructs pRic1, pRic2 and pRic3 were transformed into *A. tumefaciens* strain LBA4404 using a triparental mating method as follows. Freshly grown cultures of *E. coli* Top10 containing pric1, pRic2 or pRic3, *E. coli* Top10 containing the helper plasmid pRK2013 and *A. tumefaciens* LBA4404 were mixed in the middle and streaked to the edges of a LB plate which was then incubated overnight at 25° C. A loop of cells from the LB plate was then streaked onto a fresh LB agar plate containing rifampicin (200 μg/ml) and kanamycin (50 μg/ml) for pRic1 transformations and rifampicin (200 μg/ml), kanamycin (50 μg/ml) and ampicillin (100 μg/ml) for pRic2 and pRic3 transformations. This plate was incubated at 25° C. until single colonies started to form (these single colonies represent *A. tumefaciens* LBA4404 containing pRic1, pRic2 or pRic3).

1.2.4 Plasmids pMB2 and pMB3

The homologous pyrG gene from wild type AF293 was amplified using primers designed to the start of the promoter and end of the terminator of the *A. fumigatus* pyrG gene (Weidener, G. and d'Enfert, C. (1998) Current Genetics 33, 378-385).

Primers AFpyrG5 (5'-cta cct cga gaa ttc gcc tca aac-3'; SEQ ID No 25) and AFpyrG3 (5'-ggc gac gaa ttc tgt ctg aga g-3'; SEQ ID No 26) were used in PCR reactions containing Taq polymerase (ABGene) and Expand Pfu polymerase (Roche Molecular Systems).

Reactions which amplified the predicted 1.9 kb fragment were cloned directly. Where Taq polymerase was used, fragments were cloned directly into PCR cloning vector pTT (Genpak Ltd, see FIG. 8). Where Expand Pfu was used, fragments were first treated with Taq polymerase for 10 min at 72° C. Reactions were then passed through a cleanup column (Qaigen Ltd) to remove residual enzymes and nucleotides and then cloned into vector pCR2.1 (Invitrogen Ltd, see FIG. 9) according to the manufacturers instructions.

In both cases ligated vector/insert were transformed into Top10 electrocompetent cells (Invitrogen Ltd) and plated onto LB agar containing ampicillin (100 μg ml). Following overnight incubation at 37° C. six individual colonies from each reaction were sub-cultured into LB broth containing ampicillin (100 μg ml). After overnight incubation at 37° C., plasmids were extracted using Qaigen Spin Mini plasmid extraction kits and digested with EcoRI.

Plasmids containing the predicted 1.9 kb insert released by EcoRI digestion were deemed positive clones. Aliquots of selected positive clones were sequenced to confirm the presence of the *A. fumigatus* pyrG gene. Sequencing was performed by MWG Biotech UK Ltd (Waterside House, Peartree Bridge, Milton Keynes, MK63BY).

Plasmid pMB2 (see FIG. 10) was generated from a Taq polymerase clone inserted into pTT. Plasmid pMB3 (see FIG. 11) was generated from a Pfu polymerase clone inserted into pCR2.1.

1.3 Isolation of *A. fumigatus* Haploid Auxotrophs 1.3.1 Nitrate Assimilation Mutants (niaD− and cnx−)

Haploid strains of *A. fumigatus* AF293 were identified which were deficient in the utilisation of nitrogen in the form of nitrate. Nitrate mutants were selected after inoculation of AF293 conidia ($10^7$ per plate) on chlorate plates (600 mM sodium chlorate) supplemented with 10 mM asparagine. Colonies growing on chlorate plates were characterised further by their ability to grow on agar containing either 10 mM nitrate, 10 mM nitrite or 10 mM hypoxanthine as the sole nitrogen source. Colonies unable to utilise nitrate alone were classified as niaD− mutants. Colonies unable to utilise nitrate or hypoxanthine were classified as cnx− mutants. Reversion rates were checked by plating conidia onto nitrate media at $10^7$ conidia/ml. No reversion was seen at this level.

1.3.2 pyrG− Mutants

The pyrG− phenotype is due to a mutation in the gene encoding orotidine 5-phosphate decarboxylase. This causes a requirement for supplementation of the growth media with 10 mM uracil and 10 mM uridine in order to allow pyrG− mutants to grow.

Generation of pyrG− mutants is achieved by the use of the metabolic inhibitor fluoroorotic acid (FOA). FOA is added to complete media (CM agar) at a concentration of 1 mg/ml. CM contains in grams per litre: malt extract, 20; glucose, 10; peptone, 1; agar, 15.

A. fumigatus spores are spread onto CM/FOA plates at a concentration of $10^7$ and $10^8$ per plate. Plates are incubated at 37° C. until colonies appear (usually 3-5 days). Colonies are then picked onto CM/FOA replica plates for purity and to prepare for confirmation of the nutritional status.

Confirmation of apyrG$^-$ phenotype is achieved by checking the requirement for uracil/uridine in the growth media. Two sets of minimal media (MM) are prepared, one supplemented with uracil/uridine (10 mM each final concentration) and one with no supplementation. MM contains in grams per litre: $NaNO_3$, 6.0; $KH_2PO_4$, 1.52; KCl, 0.52; $MgSO_4.7H_2O$, 0.52; glucose, 10.0; trace element solution, 1.0 ml; media is adjusted to pH 6.5 with KOH. Trace element solution contains in grams per litre: $FeSO_4$, 1.0; $ZnSO_4.7H_2O$, 8.8; $CuSO_4.5H_2O$, 0.4; $MnSO_4.4H_2O$, 0.15; $Na_2B_4O_7.10H_2O$, 0.1; $(NH_4)_6Mo_7O_{24}.4H_2O$, 0.05. Uracil is quite insoluble and is made at 20 mM stock in water, uridine is made up at 500 mM stock in water. Both solutions are filter sterilised. CM and MM are made up and autoclaved in small volumes in order to compensate for the large volume of uracil which needs to be added (due to its low solubility).

Suspected pyrG$^-$ mutants are replica plated onto the two agars and incubated at 37° C. True pyrG$^-$ mutants should emerge within 48 h on plates supplemented with uracil/uridine and no growth should occur on the corresponding plate containing no supplementation.

1.3.3 Isolation of Haploid Double Auxotrophs (pyrG$^-$/niaD$^-$ and pvrG$^-$/cnx$^-$)

The isolation of haploid double auxotrophs (pyrG$^-$/niaD$^-$ and pyrG$^-$/cnx$^-$) is necessary for the production of diploids containing a double pyrG$^-$/pyrG$^-$ (phenotype. The resulting pyrG$^-$/pyrG$^-$ diploids can then be used in transformation experiments utilising plasmids pRic3, ppyrG, pMB2 and pMB3 all of which use the pyrG gene as a marker for DNA integration.

Using a haploidpyrG mutant (produced as in section 1.3.2) as the parental strain the exact protocol was followed as in section 1.3.1 (Nitrate assimilation mutants (niaD$^-$ and cnx$^-$)). In this case all media used for the selection and confirmation of nitrate assimilation mutants was supplemented with uracil/uridine (10 mM each final concentration) due to the presence of the pyrG$^-$ phenotype.

The order of making the double auxotrophs was found to be important. Starting with a niaD$^-$ or cnx$^-$ mutant as the parental strain we were unable to then isolate a niaD$^-$/pyrG$^-$ or cnx$^-$/pyrG$^-$ double mutant. All our double mutants were made using a haploidpyrG$^-$ mutant as the parental strain.

1.4 Production of Diploids in A. fumigatus:

These methods are based around a paper published by Strømnæs and Garber in 1963 (Strømnæs, Ø and Garber, E. D. (1963) Genetics 48, 653-662). Using the following methods diploid strains can be produced which are either (niaD$^-$/cnx$^-$) when using single auxotrophic markers or (pyrG$^-$/pyrG$^-$/niaD$^-$/cnx$^-$) when using double auxotrophic markers. Diploids with the niaD$^-$/cnx$^-$ phenotype are used in transformation experiments which utilise hygromycin resistance as a marker for DNA integration. Diploids with the pyrG$^-$/pyrG$^-$/niaD$^-$/cnx_ phenotype are used in transformation experiments which utilise the pyrG gene as a marker for DNA integration.

1.4.1 Frontier Method

This is our method of choice for the production of diploids in A. fumigatus. Spores from niaD$^-$ and cnx$^-$ mutants, or niaD$^-$/pyrG$^-$ and cnx$^-$/pyrG$^-$ mutants (both at $10^6$ conidia per ml) were each inoculated on to one half of an agar plate containing Vogel's agar (Vogel, H. J. (1956) which is a convenient growth medium for Neurospora (medium N) Microbiol. Gen. Bull. 13: 42-44). Plates were incubated at 28° C. until the colonies had developed sufficiently to merge. Conidia were collected from mycelia at the junction of the two colonies. Conidia were plated onto media containing nitrate (10 mM) as the sole nitrogen source and incubated at 37° C. until colonies had developed. Colonies growing at this stage were regarded as presumptive diploids. The leading edge of growing colonies were transferred to fresh nitrate media and allowed to develop. Conidia from these colonies were then transferred to nitrate media and incubated at 37° C.

During the initial step of this method the plates are incubated at 28° C. as opposed to 37° C. Incubation at the lower temperature slows down the growth rate, increasing the chance of heterokaryon formation and the subsequent production of diploids.

When double auxotrophs were used to produce diploids all media was supplemented with uracil/uridine (10 mM each final conc) due to the presence of the pyrG$^-$ phenotype.

1.4.2: Mat Method

Conidia from both niaD$^-$0 and cnx$^-$ mutants, or niaD$^-$/pyrG$^-$ and cnx$^-$/pyrG$^-$ mutants were collected and counted. Fifty μl of conidia (approximately $1\times10^6$ per ml) from each mutant phenotype was mixed with 200 μl of complete medium (CM broth) and incubated overnight at 37° C. CM broth contains in grams per litre of water: malt extract, 20; bacto-peptone, 1; D-glucose, 20 (Rowlands & Turner. (1973) Molecular and General Genetics 126: 201-216.). The resulting mycelial mat was placed on minimal media containing 10 mM nitrate as the sole nitrogen source and incubated at 37° C. until growth had occurred. Subcultures of any outgrowths of the primary inoculum were taken by removing sections of the leading edge and transferring to fresh nitrate medium. Growth on this media indicates a stable diploid colony.

The ability to grow on nitrate media indicated the formation of a diploid colony since neither the niaD$^-$ or cnx$^-$ (nor niaD$^-$/pyrG$^-$ or cnx$^-$/pyrG$^-$) mutants can grown on this media. Therefore, any colony growing on nitrate must have a functional gene i.e. obtained through genetic fusion of the two mutants.

When double auxotrophs were used to produce diploids all media was supplemented with uracil/uridine (10 mM each final conc) due to the presence of the pyrG$^-$ phenotype.

1.4.3: Protoplast Fusion

Conidia ($10^9$ total) from niaD$^-$ and cnx$^-$ mutants, or niaD$^-$/pyrG$^-$ and cnx$^-$/pyrG$^-$ mutants were inoculated into 100 ml Vogel's medium and incubated for 16 h at 37° C. Germlings were harvested by filtration and suspended in 50 ml protoplasting buffer, PB (1M NaCl, 10 mM CaCl) containing lysing enzyme at 2 mg/ml. Cultures were incubated at 30° C. with constant shaking (100 rpm) for 30-90 min. Protoplast formation was monitored microscopically until around 80-90% of germlings were converted to protoplasts. Protoplasts were harvested by filtration, concentrated by centrifugation (2000 g for 5 min) washed in PB and resuspended in sorbitol buffer (0.9M sorbitol, 0.125M EDTA pH 7.5). Protoplasts were diluted to a concentration of $10^7$ per ml. Equal amounts (100 μl) of protoplasts from both niaD⁻ and cnx⁻ mutants, or niaD⁻/pyrG⁻ and cnx⁻/pyrG⁻ mutants were mixed with 100 µl of 30% PEG and placed on ice for 20 min.

100 µl and 50 µl aliquots were added to tempered nitrate media (10 mM nitrate final) supplemented with 1.2M sorbitol and 10 mM CaCl. Plates were incubated at 30° C. until colonies emerged. Colonies were transferred to fresh nitrate medium and allowed to develop.

When double auxotrophs were used to produce diploids all media was supplemented with uracil/uridine (10 mM each final concentration) due to the prescience of the pyrG⁻ phenotype.

1.5 Production of Diploids in *C. glabrata*:

*C. glabrata* is naturally haploid but diploid strains may be produced as follows.

Suitable parental *C. glabrata* haploid strains are selected which have lost the ability to make specific metabolites or enzymes. Parental strains may be selected by screening for natural spontaneous mutations or by inducing mutation through UV mutagenesis or treatment with chemical mutagens e.g. nitric acid.

Where spontaneous mutations are used, the desired mutations are screened by plating liquid cultures of *C. glabrata* onto solid complete media which may contain vitamin and mineral supplements to allow for growth of desired mutant phenotypes.

Colonies are then replica plated on to minimal media which are deficient in one particular nutrient only. Mutant auxotrophs can then be identified by comparing their is growth on both complete and minimal media. Organisms which fail to grow on minimal media but grow on supplemented complete media are classified as auxtrophic for the deficient compound. It is preferable that one parent is auxotrophic for two compounds preferably from uracil, arginine, leucine, histidine and adenine and that the other parent is also auxotrophic for two of the said compounds but its auxotrophy differs from the other parent.

Formation of diploid *C. glabrata* may be achieved by joint culture of two parental auxotrophs in liquid media containing the necessary nutrients for both parents to grow. This is followed by sub-culturing organisms from this media to minimal media deficient in the auxotrophic nutrients of either parent. Diploid strains can then be isolated from this media.

Additionally diploid strains may be formed from haploid parental auxotrophs by polyethylene glycol (PEG) mediated protoplast fusion. Protoplasts from each parental haploid auxotroph are formed by digestion of the cell wall with a suitable commercial protoplasting enzyme (the preferred enzyme being Zymolase). Protoplasts from each haploid parent are mixed (the joint culture stage) in the presence of PEG. Protoplasts are then plated onto solid minimal medium deficient in auxotrophic nutrients of the parent haploid strains but supplemented with an osmotic stabiliser to prevent protoplast bursting. Prototrophic colonies that derive from this minimal media are presumptive diploids.

1.6 Re-Haploidisation

The following method was used for the re-haploidisation of diploid colonies of *C. glabrata* and *A. fumigatus*. Diploid colonies were subjected to re-haploidisation by the use of the mitotic inhibitor fluorophenylalanine (FPA).

Conidia (*A. fumigatus*) or cells (*C. glabrata*) were collected from stable diploid colonies and spread plated onto complete media containing nitrate and 0.01-0.2% FPA and incubated at 37° C. for 3 days or until rapidly growing sectors emerged (*A. fumigatus*). Conidia were collected from each sector (*A. fumigatus*) or colonies picked (*C. glabrata*) and plated onto nitrate, nitrite and hypoxanthine media and the nitrogen utilisation profiles of the resulting conidia (*A. fumigatus*) or cells (*C. glabrata*) assessed. Colonies with the nitrogen utilisation profiles of the parental strains could then be re-isolated indicating a haploid.

1.7 Transformation Experiments:

1.7.1 Electroporation

This is our method of choice for the production of transformants in *A. fumigatus*.

Approximately 125 ml of YG (0.5% (w/v) yeast extract, 2% (w/v) glucose, 5 mM each uridine and uracil) medium was inoculated with 10⁹ conidia from an auxotrophic haploid or diploid strain. The preferred auxotrophic strains were derived from AF300 or AF293.

For transformation of swollen conidia, cultures were incubated for 4 h at 37° C. with constant shaking (200 rpm). For transformation of germlings, incubation was for 8 h again at 37° C. Swollen spores or germlings were collected by centrifugation (5 min at 5000×g) and washed in 200 ml of ice cold sterile water. Spores or germlings were resuspended in 10-12 ml of YED (1% (w/v) yeast extract, 1% (w/v) glucose, 20 mM HEPES, pH 8.0), and incubated at 30° C. for a further 60 min. Spores/germlings were collected by centrifugation as described and resuspended in 1 ml of EB buffer (10 mM Tris pH 7.5, 270 mM sucrose, 1 mM lithium acetate).

Electroporation was carried out in 50 µl aliquots of spores/germlings (5×10⁷ germlings/conidia). 50 µl of swollen conidia/germlings were transferred to an electroporation cuvette, on ice, and 1-5 µg of transforming DNA added. This may be in the form of circular or linearised plasmid ppyrG, pMB2, pMB3 or another plasmid or DNA species carrying a complimentary DNA sequence to the auxotrophic markers of the recipient strain.

Conidia/germlings and transforming DNA were mixed and left on ice for 30 min. Conidia/germlings were electroporated in a Gene Pulser II instrument (Bio-Rad Ltd) set at 1 kV, 400 Ω and 25 ΞF.

1 ml of cold YED was added to the cuvette and incubated at 37° C. for 1 h. Aliquots were spread on non-selective agar (Vogel's, minimal media or complete media) without urine or uracil. Colonies growing on non-selective media were deemed putative transformants.

1.7.2 PEG-Mediated Protoplast Transformation

The following method is used for transformation of protoplasts of *C. glabrata* which are produced as described in section 1.5, and *A. fumigatus* as herein described below.

Conidia (*A. fumigatus*) from AF293 pyrG strains with additional niaD⁻ or cnx⁻ auxotrophy were cultured on solid CM media supplemented with 10 mM uracil and 10 mM uridine at 37° C. for 2-4 days. Conidia were collected in 10 ml PBS/0.1% (w/v) Tween 80 and counted using a heamocytometer. 1×10⁷ conidia were inoculated into 50 ml Vogel's media in Erlinmeyer flasks, again supplemented with 10 mM uracil and 10 mM uridine. Flasks were incubated overnight at 37° C. with constant shaking and the resultant mycelia was harvested by vacuum filtration. Mycelia was resuspended in 20 ml protoplasting buffer (1M NaCl, 10 mM MgCl₂) and protoplasting enzyme (zymolase) added to a final concentration of 1-5 mg/ml. This mycelia/enzyme suspension was incubated at 30° C. with gentle shaking (80 rpm) and protoplast generation followed microscopically over a maximum 3 h period. Protoplasts were harvested when most of the mycelia had been converted to protoplasts by filtration through sterile gauze.

Protoplasts were pelleted by gentle centrifugation (800 g×5 min) and washed 2×10 ml in protoplasting buffer before finally being resuspended in stabili sing buffer (0.9 M sorbitol, 0.1 M EDTA) to a final concentration of $2\times10^7$ protoplasts/ml. Up to 2 μg of linearised transforming plasmid (either ppyrG, pMB2 or pMB3) was added to the protoplast suspension and placed on ice for 30 min.

500 μl PEG 3000 (40% (w/v)) was added dropwise to 500 μl protoplast/plasmid suspension containing $10^7$ protoplasts. This PEG protoplast suspension was incubated on ice for a further 15 min before centrifugation at 100 g for 10 min. The supernatant was removed and replaced with 500 μl of stabilising buffer. Transformation reactions were either plated onto the surface of Vogel's agar plates containing 1% (w/v) glucose, 1.2 M sorbitol or mixed with 20 ml of molten tempered (to 40-45° C.) of the same agar.

Plates were incubated at 37° C. for up to 14 days and inspected for growth. Colonies growing on this selection media were deemed putative transformants.

1.7.3 *Agrobacterium*-Mediated Transformation

The *A. tumefaciens* strains containing the vectors pRic1, pRic2 or pRic3 were grown at 29° C. overnight on LB plates containing: rifampicin, kanamycin, ampicillin and gentamicin for *A. tumefaciens* GV3101 containing pRic2 or pRic3; rifampicin, kanamycin and gentamicin for *A. tumefaciens* GV3101 containing pRic1; rifampicin and kanamycin for *A. tumefaciens* LBA4404 containing pRic1; rifampicin, kanamycin and ampicillin for *A. tumefaciens* LBA4404 containing pRic2 or pRic3. All antibiotic concentrations are as stated in the Plasmid construction section (1.2.3) except for gentamicin at 20 μg/ml. A single colony was streaked on a minimal medium plate. Minimal medium (MM) contains in grams per litre: $K_2HPO_4$, 2.05; $KH_2PO_4$, 1.45; NaCl, 0.15; $MgSO_4.7H_2O$, 0.50; $CaCl.6H_2O$, 0.1; $FeSO_4.7H_2O$, 0.0025; $(NH_4)_2SO_4$, 0.5; glucose, 2.0. The plates were incubated at 29° C. for 1 to 2 days.

Several colonies were inoculated in minimal medium containing the appropriate antibiotics and grown at 29° C. overnight. After dilution of *A. tumefaciens* cells to an $OD_{660nm}$ of approx. 0.15 in induction medium the culture was grown for 6-7 hours at 29° C. The induction medium (IM) differs from MM in that the 2 grams per litre glucose was replaced by 10 mM glucose and 40 mM MES (pH 5.3), 0.5% glycerol (w/v) and 200 μM acetosyringone (AS) were added. In order to confirm that the transformation of *A. fumigatus* by *A. tumefaciens* is dependent on T-DNA transfer, a negative control was included in which the vir inducer AS was omitted.

Conidia were obtained by growing the *A. fumigatus* strains (haploid or diploid) at 37° C. on Vogel's minimal medium agar plates for several days and subsequently washing the surface of the plates with physiological salt solution and then filtering the conidial suspension through glass wool.

For transformation of conidia, conidia were diluted in physiological salt solution at a concentration of $10^6$ or $10^7$ conidia per ml and 100 μl was mixed with 100 μl of the *A. tumefaciens* culture (induced as detailed using IM). Subsequently, the mixtures were plated on nitrocellulose filters placed on absorbent pads containing IM (reduced glucose concentration to 5 mM) and incubated at 25° C. for 2 to 3 days. The negative control samples were incubated on IM pads in which the vir inducer AS was omitted. After this incubation period, the filters were transferred to Vogel's medium agar plates containing cefotaxime (200 μM) to kill the *A. tumefaciens* cells and hygromycin (400 μg/ml) to select for fungal transformants.

1.7.4 Early Identification of Transformants

Using the previously described transformation methods it was found beneficial to be able to identify transformants at the earliest possible stage of their development. Putative transformants were identified using a stereo microscope (Zeiss Ltd) when they were not yet visible to the naked eye and were picked using a sterile, fine gauge needle and transferred to individual petri dishes containing selective agar.

1.8 DNA Isolation, PCR and Southern Analysis:

To obtain mycelial material for genomic DNA isolation, approximately $10^7$ *A. fumigatus* conidia were inoculated in 50 ml of Vogel's minimal medium and incubated with shaking at 200 rpm until late exponential phase (18-24 h) at 37° C. The mycelium was dried down onto Whatmann 54 paper using a Buckner funnel and a side-arm flask attached to a vacuum pump and washed with 0.6 M $MgSO_4$. At this point it is possible to freeze-dry the mycelium for extraction at a later date. The mycelium (fresh or freeze dried) was ground to a powder using liquid nitrogen in a −20° C. cooled mortar. The powder was added to a 1.5 ml microcentrifuge tube using an ethanol-cleaned spatula (no more than 0.4 ml), 0.6 ml of extraction buffer (0.7 M NaCl; 0.1 M $Na_2SO_3$; 0.1 M Tris-HCl pH 7.5; 0.05 M EDTA; 1%(w/v) SDS) heated to 65° C. was added and the microfuge tube was incubated at 65° C. for 20 min. 0.6 ml of chloroform/isoamyl alcohol (24:1) was added, the tube was vortex mixed thoroughly and incubated on ice for 30 min. The tube was centrifuged at 12,000×g for 30 min and the aqueous phase carefully transferred to a fresh microfuge tube without disturbing the interface. An equal volume of isopropanol was added, mixed by inversion and incubated at room temperature for 10 minutes. The tube was centrifuged at 2000×g for 5 min, the supernatant was removed and the pellet allowed to air dry. The pellet was suspended in 200 μl of 18 MΩ water and incubated at 37° C. for 15-30 min. 100 μl of 7.5 M ammonium acetate was added, mixed by inversion and incubated on ice for 1 hour. The tube was centrifuged at 12000×g for 30 min, the supernatant transferred to a fresh tube and 0.54 volumes of isopropanol were added, mixed by inversion and incubated at room temperature for 10 minutes. The tube was centrifuged at high speed for 5 min, the supernatant was removed and the pellet washed in 500 μl of 70% ethanol. The tube was centrifuged at high speed for 5 min and all the ethanol was removed. The pellet was air dried and suspended in 100 μl of TE (10 mM Tris-HCl pH 7.5; 1 mM EDTA) or 18 MΩ water. The DNA was treated with RNase A (1 μl of 1 mg/ml stock) before use.

To confirm the transformation of *A. fumigatus* with plasmid DNA containing the pyrG gene (ppyrG, pRic3, pMB2 and pMB3) we subjected the purified DNA from transformed fungal colonies to PCR and southern analysis.

PCR was carried out using the following primers:

pyrG1:
5'-gca gag cga ggt atg tag gc-3';    (Seq ID No 20)

pyrG2:
5'-aag ccc tcc cgt atc gta gt-3';    (Seq ID No 21)

pyrG3:
5'-ata cct gtc cgc ctt tct cc-3';    (Seq ID No 22)

-continued

```
pyrG4:
5'-ttt atc cgc ctc cat cca-3'; and    (Seq ID No 23)

pyrG5:
5'-gcc ttc ctg ttt ttg ctc ac-3'.     (Seq ID No 24)
```

All the pyrG primers (pyrG1-pyrG5) were designed to pUC19 sequence which is present in the pyrG transformation cassettes. Designing primers to the actual pyrG gene would be of no diagnostic use as pryG⁻ strains still carry the pyrG sequence.

To confirm the transformation of *A. fumigatus* with T-DNA containing the hph gene from *A. tumefaciens* we subjected the purified DNA from transformed fungal colonies to PCR and southern analysis.

```
hph6:                                  (Seq ID No 1)
5'-cga tgt agg agg gcg tgg at-3';

hph7:                                  (Seq ID No 2)
5'-atc gcc tcg ctc cag tca at-3';

hph12:                                 (Seq ID No 3)
5'-ctt agc cag acg agc ggg tt-3';

hph13:                                 (Seq ID No 4)
5'-caa gac ctg cct gaa acc ga-3'; and hph14:                                 (Seq ID No 5)
5'-tcg tcc atc aca gtt tgc ca-3'.
```

For southern analysis, approximately 2.5 µg DNA was digested with a restriction enzyme which does not cut within the inserted DNA sequence for 16 hours and separated on a 0.8% agarose TAE gel. DNA was transferred to a Hybond N membrane by capillary blotting (overnight) and the membrane was pre-hybridized according to the Hybond protocol. Probes specific for the pyrG or hph gene were digoxigenin (DIG) (Feinberg, A. P. and Vogelstein, B. (1983) Analytical Biochemistry 132, 6-13) or $\alpha^{32}$P-labelled PCR products amplified using the primers detailed in this section.

1.9 Isolation of Mutated Gene Sequences 1.9.1 TAIL-PCR

As the T-DNA region of pRic1 does not contain a bacterial origin of replication, plasmid rescue (see section 1.9.2) cannot be used to isolate the mutated gene of interest. In this case we used a method described as thermal asymmetric interlaced PCR (TAIL-PCR: Liu et al. (1995) The Plant Journal 8: 457-463).

Primers were designed to the NPTII gene region of pRic1. This region of DNA is inserted into the mutated gene during transformation and hence acts as a marker for the mutated gene.

The primers used were:

```
NPT1:                                  (Seq ID No 6)
5'-tcc cgc tca gaa gaa ctc gtc aa-3';

NPT2:                                  (Seq ID No 7)
5'-ttg ggt gga gag gct att cgg ct-3';

NPT3:                                  (Seq ID No 8)
5'-tgt tgt gcc cag tca tag ccg aa-3';

NPT4:                                  (Seq ID No 9)
5'-agc cga ata gcc tct cca ccc aa-3';

NPT5:                                  (Seq ID No 10)
5'-cag att att tgg att gag agt ga-3';

AD1:                                   (Seq ID No 11)
5'-ntc ga(g/c) t(a/t)t (g/c)g(a/t) gtt-3';

AD2:                                   (Seq ID No 12)
5'-ngt cga (g/c)(a/t)g ana (a/t)ga a-3'; and AD3:                                   (Seq ID No 13)
5'-(a/t)gt gna g(a/t)a nca nag a-3'.
``` where n=any base, (x/y)=wobble position.

NPT1 and NPT2 were used to check that the NPTII sequence is present in the transformants. NPT1-NPT3 are nested primers. NPT3 is used in the primary TAIL-PCR, NPT4 in the secondary TAIL-PCR and NPT5 in the tertiary TAIL-PCR. AD1-AD3 are arbitrary degenerate primers. TAIL-PCR cycle settings were as described in the published method (Liu et al. supra). PCR fragments isolated from the tertiary TAIL-PCR by this method were cloned and sequenced by conventional molecular biological techniques.

1.9.2 Plasmid Rescue

As the T-DNA region of pRic2 and pRic3 and plasmids ppyrG, pMB2 and pMB3 all contain a bacterial origin of replication, the technique of plasmid rescue can be used to isolate the mutated gene of interest. Genomic DNA isolated from transformed *A. fumigatus* (section 1.8) was digested to completion with a restriction enzyme that does not cut within the inserted DNA. This digested DNA was then purified and re-ligated with T4 DNA ligase. The random sized, closed circular DNA molecules resulting from this process were then used to transform *E. coli* strain Top10 by electroporation using a Biorad Genepulser (2.1 kV, 200 Ω, 25 µF). Transformed cells were plated on LB agar plates containing ampicillin (100 µg/ml). These plates were incubated at 37° C. until single colonies started to form (these single colonies represent *E. coli* Top10 containing a plasmid with a bacterial origin of replication i.e. from the inserted DNA.). DNA was isolated from these cells and sequenced by conventional molecular biological techniques.

1.9.3 Inverse PCR

In a similar manner to plasmid rescue, genomic DNA isolated from transformed *A. fumigatus* was digested to completion with a restriction enzyme that does not cut within the inserted DNA. This digested DNA was then purified and re-ligated with T4 DNA ligase. Instead of being transformed into *E. coli* as in the plasmid rescue method, the random sized, closed circular DNA molecules resulting from this process were subjected directly to PCR.

This technique may be used when trying to isolate the mutated gene from transformants produced using linearised plasmids which have been cut with a known restriction enzyme. For example, we have designed primers to isolate the mutated gene of interest from transformants produced using pMB3 linearised with XbaI.

PCR was carried out using the following primers:

```
RCpyrG5:                               (Seq ID No 14)
5'-gtt tga ggc gaa ttc tc-3';

RCpyrG3:                               (Seq ID No 15)
5'-ctc tca gac aga att cgt-3';

pMB3R:                                 (Seq ID No 16)
5'-atc cat cac act ggc g-3';
```

-continued

```
T7pro:                              (Seq ID No 17)
5'-taa tac gac tca cta tag gg-3';

M13-20:                             (Seq ID No 18)
5'-gta aaa cga cgg cca g-3'; and M13-40                              (Seq ID No 19)
5'-gtt ttc cca gtc acg ac-3'.
```

1.10 Identification of Mutated Genes

All DNA sequencing was carried out by external contract (MWG Biotech UK 10 Ltd., Waterside House, Peartree Bridge, Milton Keynes, MK6 3BY). Sequence data obtained was compared to sequences in the public domain databases via BLAST searches (National Centre for Biotechnology Information.

2. Results 2.1 Haploid Transport Library

Using the protocols detailed above, the inventors transformed haploid AF300 and AF293 with *A. tumefaciens* (LBA4404 and GV3101) and have approximately 300 (MA1-MA300) transformants frozen down (−80° C.) which exhibit growth (at various radial growth rates) on hygromycin (400 μg/ml or higher). One of these transformants (MA205) was taken complete circle to show that *A. fumigatus* could be transformed using the *Agrobacterium*-mediated method and that T-DNA could be integrated at a single gene locus and that locus could be identified by DNA sequencing and homology to known genes examined by the use of bioinformatics.

*A. fumigatus* transformant MA205 was produced by the transformation of AF300 with *A. tumefaciens* GV3101 containing pRic1. PCR with primers hph6 and hph7 revealed that the hygromycin gene was present in the genomic DNA. Because pRic1 does not contain a bacterial origin of replication (this origin is present in pRic2 and pRic3 by the introduction of pUC 18 DNA into the HindIII site (see section 1.2.2)) which allows the isolation of genic DNA sequences (disrupted gene etc) flanking the inserted T-DNA by plasmid rescue, we used a flanking region isolation method known.

As TAIL PCR (see section 1.9.1). The DNA fragment isolated by this method was sequenced by MWG Biotech UK Ltd. (see SEQ ID No. 27) and was translated in all six reading frames to yield a partial protein sequence of 234 amino acids. Using BLAST (National Centre for Biotechnology Information this 5 protein sequence showed strongest sequence homology (41% at the amino acid level) to a hypothetical 35.1 KD protein in the NAMS-GARI intergenic region of *Saccharomyces cerevisiae* (sp/P38805/YH08 YEAST and see FIG. 12).

Transformation of haploid AF293 using the preferred electroporation method has yielded transformants which are pyrG$^+$ by their growth on non selective media (see section 1.7.1) and which have been confirmed as true transformants by diagnostic PCR (see section 1.8). Southern blots of some of these transformants indicating the presence of random, single and/or multiple insertion events is shown in FIG. 13 (lanes A-F).

2.2 Diploid General Library:

We have produced AF293 and AF300 diploids using the above-described methods (see section 1.4) and have shown that these are in fact true *A. fumigatus* diploids via re-haploidisation with the use of the mitotic inhibitor fluorophenylalanine (FPA) (see section 1.6).

These diploids were used to form mutant banks according to the present invention utilising the transformation methods detailed in section 1.7. Diploid transformants have been isolated which are pyrG$^+$ by their growth on non selective media and which have been confirmed as true transformants by diagnostic PCR. A southern blot showing an example of a single integration event in a diploid transformant is shown in FIG. 13 (lane G).

What is claimed is:

1. A method of selecting a microorganism clone with a mutation in an essential gene comprising:
   (i) providing a mutant bank of diploid microorganism cells comprising a population of diploid microorganism cells in which mutations have been randomly induced, wherein at least one cell has a random mutation which is lethal to the haploid form of the cell;
   (ii) exposing the diploid microorganisms to an agent that induces the microorganisms into haploid form; and
   (iii) selecting a diploid clone for which the haploid microorganism is not viable, the non-viability indicating that the selected clone has a mutation in an essential gene, wherein the microorganism is *Aspergillus fumigatus*.

2. The method according to claim 1 which further comprises identifying the mutated gene in the selected microorganism clone.

3. The method according to claim 1, wherein in the mutant bank a plurality of cells in the population each individually have a mutation which disrupts the activity of at least one gene, so that collectively the said plurality of cells have mutations in a plurality of genes within the genome.

4. The method according to claim 3, wherein the said plurality of genes makes up 10% of the genes within the genome.

5. The method according to claim 3, wherein the said plurality of genes makes up all the genes of the genome of the microorganism.

6. The method according to claim 1, wherein the mutant bank is formed by an insertional mutagenesis method, wherein a DNA molecule is inserted into each gene to cause the mutation.

7. The method according to claim 6, wherein the DNA molecule is selected from the group consisting of a selectable marker, a pyrG gene, a pyrG gene from *A. fumigatus*, a pyrG gene harboured on a plasmid and an *Aspergillus* pyrG gene harboured on a plasmid.

8. A method of generating a mutant bank of microorganisms comprising a population of mutant *A. fumigatus* cells in which mutations have been randomly induced, wherein at least one cell has a random mutation that disrupts the activity of at least one gene, said method comprising the steps of:
   (i) culturing a population of *A. fumigatus* cells; and
   (ii) inducing a random mutation in at least one cell of the population which mutation disrupts the activity of at least one gene in the genome of the cell, said cells being diploid and being inducible into haploid form.

9. A method according to claim 8, wherein the mutant bank is formed by an insertional mutagenesis method, wherein a DNA molecule is inserted into each gene to cause the mutation.

10. A method according to claim 9, wherein the DNA molecule is selected from the group consisting of a selectable marker, a pyrG gene, a pyrG gene from *A. fumigatus*, a pyrG gene harboured on a plasmid and an *Aspergillus* pyrG gene harboured on a plasmid.

11. A method according to claim 9, wherein the DNA is introduced into the microorganism by a method selected from the group consisting of electroporation, protoplast transformation, PEG-mediated transformation and Agrobacterium-mediated transformation.

12. A method according to claim 8, wherein the diploid microorganism is a mutant for the pyrG phenotype.

13. A method according to claim 12, wherein the diploid mutant microorganism is generated using the following steps:
   (i) isolating a first haploid mutant comprising a first auxotrophic marker wherein the first auxotrophic marker results in the pyrG⁻ phenotype;
   (ii) isolating a second haploid mutant using the first haploid mutant isolated in step (i), said second mutant comprising the first pyrG⁻ auxotrophic marker and a second auxotrophic marker;
   (iii) isolating a third haploid mutant using the first haploid mutant isolated in step (i), said third mutant comprising the first pyrG⁻ auxotrophic marker and a third auxotrophic marker; and
   (iv) mating the second and third haploid mutants isolated in steps (ii) and (iii) to generate the diploid mutant exhibiting the pyrG⁻ phenotype.

14. A method according to claim 13, wherein the second and third auxotrophic markers are selected from niaD⁻ or cnx⁻.

15. A method according to claim 13, wherein step (iv) of the method comprises use of the Frontier method, Mat method or protoplast fusion for the production of diploid microorganisms in *A. fumigatus*.

16. A method according to claim 13, wherein the haploid mutants are incubated at a temperature in a range selected from the group consisting of 20 to 36° C., 24 to 33° C. and 26 to 30° C.

17. A mutant bank of diploid microorganisms comprising a population of mutant cells in which each individual cell has a random mutation that disrupts the activity of one gene, said population collectively having a mutation in every gene within the genome and wherein the mutant bank may be induced into haploid form, wherein the microorganism is *A. fumigatus*.

* * * * *